(12) United States Patent
Candau et al.

(10) Patent No.: US 8,241,613 B2
(45) Date of Patent: Aug. 14, 2012

(54) SUN PROTECTION COMPOSITIONS COMPRISING SEMI-CRYSTALLINE POLYMERS AND HOLLOW LATEX PARTICLES

(75) Inventors: Didier Candau, Bievres (FR); Karl Boutelet, Paris (FR)

(73) Assignee: L'Oreal, Paris (FR)

( * ) Notice: Subject to any disclaimer, the term of this patent is extended or adjusted under 35 U.S.C. 154(b) by 966 days.

(21) Appl. No.: 12/216,527

(22) Filed: Jul. 7, 2008

(65) Prior Publication Data
US 2009/0041691 A1   Feb. 12, 2009

Related U.S. Application Data

(60) Provisional application No. 60/929,964, filed on Jul. 19, 2007.

(30) Foreign Application Priority Data

Jul. 6, 2007 (FR) ...................................... 07 56322

(51) Int. Cl.
- *A61K 8/72* (2006.01)
- *A61K 8/81* (2006.01)
- *A61Q 17/04* (2006.01)

(52) U.S. Cl. .......................................... 424/59; 424/60
(58) Field of Classification Search .................. None
See application file for complete search history.

(56) References Cited

U.S. PATENT DOCUMENTS

| 2004/0005279 A1 | 1/2004 | Lorant et al. |
| 2006/0292095 A1* | 12/2006 | Biatry et al. .................... 424/59 |

FOREIGN PATENT DOCUMENTS

| EP | 0 669 124 A1 | 8/1995 |
| EP | 0 893 119 A1 | 1/1999 |
| EP | 1 092 421 A2 | 4/2001 |
| EP | 1 331 000 A1 | 7/2003 |
| WO | WO 2006/048159 A1 | 5/2006 |

OTHER PUBLICATIONS

French Search Report corresponding to FR 0756322, issued on Feb. 20, 2008, 2 pages.

* cited by examiner

*Primary Examiner* — James H Alstrum Acevedo
*Assistant Examiner* — Daniel L Branson
(74) *Attorney, Agent, or Firm* — Buchanan Ingersoll & Rooney PC

(57) ABSTRACT

Topically applicable cosmetic/dermatological UV protection compositions having enhanced SPF contain at least one organic UV screening agent and/or at least one inorganic screening agent, such compositions also containing at least the following constituents (A) and (B):
- A) a semi-crystalline polymer which is solid at ambient temperature and has a melting point of greater than or equal to 30° C., containing a) a polymeric backbone and b) at least one crystallizable organic side chain and/or one crystallizable organic block forming part of the backbone of this said polymer, said polymer having a number-average molecular mass Mn of greater than or equal to 1,000, and
- B) hollow latex particles having a particle size ranging from 150 to 380 nm, formulated into a topically applicable, physiologically acceptable medium therefor.

15 Claims, No Drawings

SUN PROTECTION COMPOSITIONS COMPRISING SEMI-CRYSTALLINE POLYMERS AND HOLLOW LATEX PARTICLES

CROSS-REFERENCE TO PRIORITY/PROVISIONAL APPLICATIONS

This application claims priority under 35 U.S.C. §119 of FR 0756322, filed Jul. 6, 2007, and of U.S. Provisional Application No. 60/929,964, filed Jul. 19, 2007, each hereby expressly incorporated by reference and each assigned to the assignee hereof.

BACKGROUND OF THE INVENTION

1. Technical Field of the Invention

The present application relates to cosmetic or dermatological compositions comprising at least one organic UV screening agent and/or at least one inorganic screening agent, said compositions comprising, formulated into a physiologically acceptable medium, at least the following constituents (A) and (B):

A) a semi-crystalline polymer which is solid at ambient temperature and has a melting point of greater than or equal to 30° C., containing a) a polymeric backbone and b) at least one crystallizable organic side chain and/or one crystallizable organic block forming part of the backbone of the said polymer, the said polymer having a number-average molecular mass Mn of greater than or equal to 1,000, and B) hollow latex particles having a particle size ranging from 150 to 380 nm.

The present invention also relates to cosmetic applications of the said compositions for topical administration which is useful to protect the skin, lips, nails, hair, scalp, lashes or brows against the deleterious effects of UV radiation, more particularly solar radiation, such compositions comprising at least one organic UV screening agent and/or at least one inorganic UV screening agent, as agents for increasing the sun protection factor (SPF) thereof.

2. Description of Background and/or Related and/or Prior Art

It is known that rays of light with wavelengths of from 280 nm to 400 nm permit tanning of the human epidermis and that, moreover, rays with wavelengths of from 280 nm to 320 nm, which are known under the trademark UV-B, give rise to erythemas and skin burns that can harm the development of a natural tan; this UV-B radiation must therefore be screened out.

It is also known that UV-A rays, with wavelengths of from 320 to 400 nm, which give rise to the tanning of the skin, are capable of inducing impairment thereof, especially in the case of sensitive skin or of skin that is continually exposed to solar radiation. The UV-A rays more particularly give rise to a loss of elasticity in the skin and to the appearance of wrinkles, leading to premature aging. This radiation promotes the onset of the erythemal reaction or amplifies that reaction in certain individuals, and may even be a cause of phototoxic or photoallergic reactions. It is therefore desirable to screen out UV-A radiation as well.

Numerous cosmetic compositions suited for the photoprotection (UV-A and/or UV-B) of the skin have been proposed to date.

These anti-sun compositions are often in the form of an oil-in-water or water-in-oil emulsion, of gels or of non-aqueous products which contain, in various concentrations, one or more insoluble and/or fat-soluble and/or water-soluble, organic and/or inorganic screening agents that are capable of selectively absorbing the harmful UV radiation. These screening agents and their amounts are selected as a function of the desired protection index. Depending on their lipophilic or, alternatively, hydrophilic character, these screening agents may become distributed, respectively, in either the fatty phase or the aqueous phase of the final composition.

For reasons of stability of these compositions and/or of tolerance on the skin, hair or mucosae, it is sometimes difficult to employ large quantities of chemical screening agents and/or mineral screening agents in order to increase the protection index of the suntan compositions. The assignee hereof has therefore sought another means of increasing the protection index of these compositions.

The efficacy of the chemical or physical screening agents is often limited by the problems of dispersal of these screening agents from the cosmetic compositions. A consequence of this is to give rise to heterogeneity in the film which is formed on the surface of the skin, which is detrimental to the quality, stability and efficacy of suntan products.

Proposals have already been made, in U.S. Pat. No. 5,663,213 and EP-1-092,421, EP-1-281,388, EP-1-281,389, EP-1-291,390 and DE10138499, to incorporate hollow latex particles in suntan formulations for the purpose of increasing their protection index.

It has also been proposed, in EP-1-331,000, that a semi-crystalline polymer be included in suntan formulations for the purpose of increasing their protection index.

SUMMARY OF THE INVENTION

Surprisingly, it has now been found that, by combining UV screening agents with a combination constituted of at least one semi-crystalline polymer and hollow latex particles, a synergy is attained in the screening power of the screening agents and, consequently, a marked improvement is obtained in the protection index (SPF or PI) of the composition comprising them, relative to a composition comprising the same screening agent or agents and the semi-crystalline polymer alone, and in relation to a composition or the same screening agents with the hollow latex particles alone. The compositions according to the invention exhibit good cosmetic properties and also good water resistance.

The present invention therefore features cosmetic or dermatological compositions comprising at least one organic UV screening agent and/or at least one inorganic screening agent, such compositions comprising, formulated into a physiologically acceptable medium at least the following constituents (A) and (B):

A) at least one semi-crystalline polymer which is solid at ambient temperature and has a melting point of greater than or equal to 30° C., containing a) a polymeric backbone and b) at least one crystallizable organic side chain and/or one crystallizable organic block forming part of the backbone of the said polymer, the said polymer having a number-average molecular mass of greater than or equal to 1,000, and B) hollow latex particles having a particle size ranging from 150 to 375 nm.

The present invention also features the cosmetic administration of the said compositions for topical application which is useful to protect the skin and/or the hair against UV radiation, more particularly solar radiation, and which compositions comprise, formulated into a physiologically acceptable medium, at least one organic UV screening agent and/or at least one inorganic UV screening agent, as agents allowing the sun protection factor (SPF) to be increased.

According to the present invention, the term "ambient temperature" means a temperature of essentially 250° C.

A "physiologically acceptable medium" means a medium which is not toxic and can be applied to the skin, lips, hair, scalp, lashes, brows, nails or any other cutaneous region of the body. The compositions of the invention may especially constitute a cosmetic or dermatological composition.

"Latex" means polymer particles in the form of an aqueous dispersion which is generally stabilized with at least one emulsifier.

The compositions may constitute, especially, a cosmetic composition. Generally speaking, a cosmetic composition is suited for contacting with the surface parts of the human body. A cosmetic suntan composition makes it possible to combat the effects of UV rays on the surface layers of the skin and especially the effects on the aging of the skin (wrinkles and fine lines).

The semi-crystalline polymer included in the compositions of the invention allows higher protection indices to be obtained without an increase in the level of chemical screening agents, and hence improves the protection index for a given quantity of screening agent. The said polymer is generally introduced into the liquid fatty phase (also referred to below as oily phase).

"Polymers" for the purposes of the invention are compounds containing at least 2 repeating structural units, preferably at least 3 repeating structural units and more especially at least 10 repeating structural units.

"Semi-crystalline polymer" for the purposes of the invention means polymers comprising a crystallizable part, a crystallizable pendant chain or crystallizable block in the backbone, and an amorphous part in the backbone, and exhibiting a first-order reversible phase-change temperature, more particularly melting (solid-liquid transition) temperature. When the crystallizable part is in the form of a crystallizable block of the polymeric backbone, the amorphous part of the polymer is in the form of an amorphous block; in that case the semi-crystalline polymer is a block copolymer, of the diblock, triblock or multiblock type, for example, comprising at least one crystallizable block and at least one amorphous block.

By "block" is meant, generally, at least 5 identical repeating structural units. In that case the crystallizable block or blocks are different in chemical nature from the amorphous block or blocks.

A "crystallizable chain or block" for the purposes of the invention is a chain or block which, on its own, would pass from the amorphous state to the crystalline state reversibly according to whether it were above or below the melting temperature. A chain for the purposes of the invention is a group of atoms which is pendant or lateral relative to the backbone of the polymer. A block is a group of atoms that belongs to the backbone, a group constituting one of the repeating units of the polymer. Advantageously the "crystallizable pendant chain" may be a chain containing at least 6 carbon atoms.

DETAILED DESCRIPTION OF BEST MODE AND SPECIFIC/PREFERRED EMBODIMENTS OF THE INVENTION

Semi-Crystalline Polymers:

The semi-crystalline polymer according to the invention has a melting temperature of greater than or equal to 30° C., preferably ranging from 30° C. to 80° C., and more preferably ranging from 30° C. to 70° C. This melting temperature is a first-order state-change temperature. This melting temperature may be measured by any known method and more particularly by using a differential scanning calorimeter (DSC).

Advantageously the semi-crystalline polymer or polymers to which the invention applies exhibit a number-average molecular mass of greater than or equal to 1,000.

Advantageously the semi-crystalline polymer or polymers of the compositions of the invention have a number-average molecular mass M n ranging from 2,000 to 800,000, preferably from 3,000 to 500,000, better still from 4,000 to 150,000, especially less than 100,000, and better still from 4,000 to 99,000. Preferably, they exhibit a number-average molecular mass of greater than 5,600, ranging for example from 5,700 to 99,000.

Preferably, the crystallizable block or blocks or chain or chains of the semi-crystalline polymers are each at least 30% of the total weight of each polymer and better still at least 40%. The semi-crystalline polymers of the invention having crystallizable blocks are block or multiblock polymers. They may be obtained by polymerization of monomer having reactive (or ethylenic) double bonds or by polycondensation. When the polymers of the invention are polymers having crystallizable side chains, these polymers are advantageously in random or statistical form.

The semi-crystalline polymers of the invention are preferably synthetic in origin. Moreover, they do not contain a polysaccharide backbone. Generally speaking, the crystallizable units (chains or blocks) of the semi-crystalline polymers according to the invention originate from one or more monomers having crystallizable blocks or chains, which are used for the preparation of the semi-crystalline polymers.

According to the invention, the semi-crystalline polymers are selected from block copolymers containing at least one crystallizable block and at least one amorphous block, the homopolymers and the copolymers bearing at least one crystallizable side chain per repeating unit, and mixtures thereof.

The semi-crystalline polymers which can be employed in the invention are more particularly:

- block polyolefin copolymers having controlled crystallization, especially those whose monomers are described in EP-A-0-951,897;
- polycondensates, and especially those of aliphatic or aromatic polyester or aliphatic/aromatic copolyester type;
- homopolymers or copolymers bearing at least one crystallizable side chain, and homopolymers or copolymers bearing in the backbone at least one crystallizable block, such as those described in U.S. Pat. No. 5,156,911;
- homopolymers or copolymers bearing at least one crystallizable side chain, more particularly having one or more fluorinated groups, such as those described in WO-A-01/19333, and mixtures thereof. In these latter two cases, the crystallizable block or blocks or side chain or side chains are hydrophobic.

Semi-Crystalline Polymers having Crystallizable Side Chains:

More particularly exemplary are those described in U.S. Pat. No. 5,156,911 and WO-A-01/19333. These are homopolymers or copolymers containing from 50% to 100% by weight of units resulting from the polymerization of one or more monomers bearing a crystallizable hydrophobic side chain.

These homopolymers or copolymers are of any kind, provided that they meet the conditions set out above.

They may result:

from the polymerization, especially free-radical polymerization, of one or more monomers having one or more double bonds which are reactive or ethylenic in relation to a polymerization, namely, a vinyl, (meth)acrylic or allyl group;

from the polycondensation of one or more monomers which bear co-reactive groups (carboxylic or sulfonic acid, alcohol, amine or isocyanate), such as, for example, polyesters, polyurethanes, polyethers, polyureas and polyamides.

Generally speaking, these polymers are selected especially from homopolymers and copolymers resulting from the polymerization of at least one monomer which has one or more crystallizable chains and may be represented by the formula X:

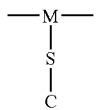

with M representing an atom of the polymeric backbone, S representing a spacer and C representing a crystallizable group.

The crystallizable chains "S—C" may be aliphatic or aromatic and optionally fluorinated or perfluorinated. "S" is especially a linear or branched or cyclic $(CH_2)_n$ or $(CH_2CH_2O)_n$ or $(CH_2O)_n$ group, with n being an integer ranging from 0 to 22. Preferably "S" is a linear group. Preferably "S" and "C" are different.

When the crystallizable chains "S—C" are aliphatic hydrocarbon chains, they comprise hydrocarbon alkyl chains having at least 11 carbon atoms and not more than 40 carbon atoms and better still not more than 24 carbon atoms. They are, especially, aliphatic chains or alkyl chains possessing at least 12 carbon atoms, and preferably they are $C_{14}$-$C_{24}$ alkyl chains. When they are fluorinated or perfluorinated alkyl chains, they contain at least 6 fluorinated carbon atoms and especially at least 11 carbon atoms of which at least 6 carbon atoms are fluorinated.

Examples of semi-crystalline polymers or copolymers having one or more crystallizable chains include those resulting from the polymerization of one or more of the following monomers: saturated alkyl (meth)acrylates with a $C_{14}$-$C_{24}$ alkyl group, perfluoroalkyl(meth)acrylates with a $C_{11}$-$C_{15}$ perfluoroalkyl group, N-alkyl(meth)acrylamides with a $C_{14}$ to $C_{24}$ alkyl group with or without a fluorine atom, vinyl esters having alkyl or perfluoro(alkyl) chains with a $C_{14}$ to $C_{24}$ alkyl group (with at least 6 fluorine atoms for a perfluoroalkyl chain), vinyl ethers having alkyl or perfluoro(alkyl) chains with a $C_{14}$ to $C_{24}$ alkyl group and at least 6 fluorine atoms for a perfluoroalkyl chain, $C_{14}$ to $C_{24}$ alpha-olefins such as, for example, octadecene, para-alkylstyrenes with an alkyl group containing 12 to 24 carbon atoms, and mixtures thereof.

When the polymers result from a polycondensation, the crystallizable hydrocarbon and/or fluorinated chains as described above are borne by a monomer which may be a diacid, a diol, a diamine or a diisocyanate.

When the polymers according to the invention are copolymers, they contain, in addition, from 0% to 50% of groups Y or Z resulting from the copolymerization:

α) of Y, which is a polar or non-polar monomer or a mixture of the two.

When Y is a polar monomer, it is alternatively a monomer which carries polyalkoxylated groups (especially ethoxylated and/or propoxylated groups), a hydroxyalkyl(meth)acrylate such as hydroxyethyl acrylate, (meth)acrylamide, an N-alkyl(meth)acrylamide, an N,N-dialkyl(meth)acrylamide such as, for example, N,N-diisopropylacrylamide, or N-vinylpyrrolidone (NVP), N-vinylcaprolactam, a monomer which carries at least one carboxylic acid group, such as (meth)acrylic, crotonic, itaconic, maleic or fumaric acids, or which carries a carboxylic anhydride group, such as maleic anhydride, and mixtures thereof.

When Y is a non-polar monomer it may be an ester of the linear, branched or cyclic alkyl(meth)acrylate type, a vinyl ester, an alkyl vinyl ether, an alpha-olefin, styrene or a styrene substituted by a $C_1$ to $C_{10}$ alkyl group, such as α-methylstyrene, or a macromonomer of the polyorganosiloxane type having vinylic unsaturation.

"Alkyl" for the purposes of the invention means a saturated group which especially is a $C_8$ to $C_{24}$ group, unless expressly mentioned, and better still a $C_{14}$ to $C_{24}$ group.

β) of Z, which is a polar monomer or a mixture of polar monomers.

In this case, Z has the same definition as the "polar Y" described above.

Preferably, the semi-crystalline polymers having a crystallizable side chain are homopolymers of alkyl(meth)acrylate or alkyl(meth)acrylamide with an alkyl group as described above, and more particularly a $C_{14}$-$C_{24}$ group, and copolymers of these monomers with a hydrophilic monomer which is preferably different in nature from (meth)acrylic acid, such as N-vinylpyrrolidone or hydroxyethyl (meth)acrylate and mixtures thereof.

B) Polymers Bearing in the Backbone at Least One Crystallizable Block:

These polymers are especially block copolymers constituted of at least two chemically different blocks of which one is crystallizable.

Exemplary are the block polymers described in U.S. Pat. No. 5,156,911;

olefin or cycloolefin block copolymers having crystallizable chains, such as those obtained from the block polymerization of:

cyclobutene, cyclohexene, cyclooctene, norbornene (i.e., bicyclo[2.2.1]hept-2-ene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8,8a-octahydronaphthalene, dicyclopentadiene or mixtures thereof, with ethylene, propylene, 1-butene, 3-methyl-1-butene, 1-hexene, 4-methyl-1-pentene, 1-octene, 1-decene, 1-eicosene or mixtures thereof, and more particularly block copoly(ethylene/norbornene)s and block (ethylene/propylene/ethylidene-norbornene) terpolymers. Also exemplary are those resulting from the block copolymerization of at least two $C_2$-$C_{16}$ and better still $C_2$-$C_{12}$ and even better still $C_4$-$C_{12}$ α-olefins, such as those referred to above, and more particularly the block bipolymers of ethylene and 1-octene.

The copolymers may be copolymers exhibiting at least one crystallizable block, the remainder of the copolymer being amorphous (at ambient temperature). These copolymers may, moreover, exhibit two crystallizable blocks differing in chemical nature. The preferred copolymers are those which at ambient temperature possess both a crystallizable block and an amorphous block, both hydrophobic and lipophilic, which are distributed sequentially; exemplary are the polymers possessing one of the following crystallizable blocks and one of the following amorphous blocks:

naturally crystallizable block: a) polyester such as poly (alkylene terephthalate)s, b) polyolefin such as polyethylenes or polypropylenes.

Amorphous and lipophilic block, for instance amorphous polyolefins or copoly(olefin)s, such as poly(isobutylene), hydrogenated polybutadiene and hydrogenated poly(isoprene).

Examples of such copolymers having a separated crystallizable block and amorphous block include the following:

α) block poly(ε-caprolactone)-b-poly(butadiene) copolymers, preferably used in hydrogenated form, such as those described in the article "Melting behavior of poly(ε-caprolactone)-block-polybutadiene copolymers" by S, Nojima, *Macromolecules*, 32, 3727-34 (1999).

β) block or multiblock hydrogenated poly(butylene terephthalate)-b-poly(isoprene) block copolymers, as cited in the article "Study of morphological and mechanical properties of PP/PBT" by B. Boutevin et al., *Polymer Bulletin*, 34, 117-23 (1995).

γ) the poly(ethylene)-b-copoly(ethylene/propylene) block copolymers that are cited in the articles "Morphology of semi-crystalline block copolymers of ethylene-(ethylene-alt-propylene)" by P. Rangarajan et al., *Macromolecules*, 26, 4640-45 (1993) and "Polymer aggregates with crystalline cores: the system poly(ethylene)-poly(ethylene-propylene)" by P. Richter et al., *Macromolecules*, 30, 1053-68 (1997).

δ) the poly(ethylene)-b-poly(ethylethylene) block copolymers that are cited in the general article "Crystallization in block copolymers" by I. W. Hamley, Advances in Polymer Science, vol. 148, 113-37 (1999).

The semi-crystalline polymers of the compositions of the invention may be non-crosslinked or partly crosslinked, with the proviso that the degree of crosslinking is not disruptive to their dissolution or dispersion in the liquid fatty phase by heating to above their melting temperature. In that case the crosslinking in question may be chemical crosslinking, by reaction with a polyfunctional monomer during the polymerization. It may also be physical crosslinking, which in that case may be due either to the establishment of hydrogen bonds or dipole bonds from groups borne by the polymer, such as, for example, dipolar interactions from carboxylate ionomers, these interactions being small in quantity and borne by the backbone of the polymer, or to phase separation from the crystallizable blocks and the amorphous blocks which are borne by the polymer.

Preferably the semi-crystalline polymers of the compositions according to the invention are non-crosslinked.

According to one particular embodiment of the invention, the polymer is selected from copolymers resulting from the polymerization of at least one monomer having a crystallizable chain and selected from saturated $C_{14}$ to $C_{24}$ alkyl(meth)acrylates, $C_{11}$ to $C_{15}$ perfluoroalkyl (meth)acrylates, $C_{14}$ to $C_{24}$ N-alkyl(meth)acrylamides with or without a fluorine atom, vinyl esters having $C_{14}$ to $C_{24}$ alkyl or perfluoroalkyl chains, vinyl ethers having $C_{14}$ to $C_{24}$ alkyl or perfluoroalkyl chains, $C_{14}$ to $C_{24}$ alpha-olefins, para-alkylstyrenes with an alkyl group containing 12 to 24 carbon atoms, with at least one ester or amide of $C_1$ to $C_{10}$ monocarboxylic acid which is optionally fluorinated, which may be represented by the formula below:

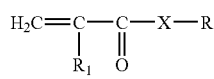

in which $R_1$ is H or $CH_3$, R is an optionally fluorinated $C_1$-$C_{10}$ alkyl group and X is O, NH or $NR_2$, where $R_2$ is an optionally fluorinated $C_1$-$C_{10}$ alkyl group.

Advantageously, the semi-crystalline polymer present in the compositions according to the invention is not a polycaprolactone.

As a particular example of a structuring semi-crystalline polymer which can be included in the compositions according to the invention, representative are the Intelimer® products by Landec which are described in the brochure "Intelimer® polymers", Landec IP22 (version 4-97). These polymers are in solid form at ambient temperature (25° C.). They bear crystallizable side chains and have the above formula X.

The semi-crystalline polymers may especially be those described in Examples 3, 4, 5, 7, 9 and 13 of U.S. Pat. No. 5,156,911, having a —COOH group resulting from the copolymerization of acrylic acid and $C_5$ to $C_{16}$ alkyl(meth)acrylate and more particularly from the copolymerization:

of acrylic acid, hexadecyl acrylate and isodecyl acrylate in a 1/16/3 weight ratio;

of acrylic acid and pentadecyl acrylate in a 1/19 weight ratio, of acrylic acid, hexadecyl acrylate and ethyl acrylate in a 2.5/76.5/20 weight ratio, of acrylic acid, hexadecyl acrylate and methyl acrylate in a 5/85/10 weight ratio, of acrylic acid and octadecyl methacrylate in a 2.5/97.5 weight ratio, of hexadecyl acrylate, polyethylene glycol methacrylate monomethyl ether containing 8 ethylene glycol units, and acrylic acid, in an 8.5/1/0.5 weight ratio.

It is also possible to employ "Structure 0" from *National Starch*, such as that described in U.S. Pat. No. 5,736,125, with a melting point of 44° C., and also semi-crystalline polymers having crystallizable pendant chains containing fluorinated groups, such as those described in Examples 1, 4, 6, 7 and 8 of WO-A-01/19333.

It is additionally possible to employ low-melting-point semi-crystalline polymers obtained by copolymerizing stearyl acrylate and acrylic acid or NVP, as described in U.S. Pat. No. 5,519,063 or EP-A-550,745, and more especially those described in Examples 1 and 2, below, which are polymer preparation examples, with a melting temperature, respectively, of 40° C. to 38° C.

It is also possible to employ semi-crystalline polymers obtained by copolymerizing behenyl acrylate and acrylic acid or NVP, such as those described in U.S. Pat. No. 5,519,063 and EP-A-550,745.

Preferably, the semi-crystalline polymers of low melting point and/or of high melting point do not contain a carboxyl group.

According to one more particular embodiment of the invention, the polymer is the product of a monomer having a crystallizable chain, selected from saturated $C_{14}$ to $C_{22}$ alkyl (meth)acrylates, and even more particularly poly(stearyl acrylate)s or poly(behenyl acrylate)s. More particularly, a selection will be made of the product Intelimer® IPA 13-1 by Landec, which is a polystearyl acrylate whose molecular weight is approximately 145,000 and whose melting temperature is 49° C.

The amount of semi-crystalline polymer in the compositions of the invention may vary widely in accordance with the desired result. The amount of semi-crystalline polymers may range, for example, from 0.1% to 50% by weight of active ingredient, preferably from 0.5% to 20% by weight of active ingredient and better still from 1% to 10% by weight of active ingredient, relative to the total weight of the composition.

Hollow Latex Particles:

The hollow latex particles according to the invention have a particle size which ranges generally from 100 to 380 nm and preferably from 150 to 375 nm and more preferably from 190 to 350 nm and more particularly from 251 to 325 nm, the particle size being measured by a Brookhaven BI-90 photon correlation spectrometer.

For a given particle size, the latex particles according to the invention must in general possess a maximum hollow fraction. The latex particles preferably contain a void fraction of 0.1% to 50% to more preferably of 5% to 50%. The void fractions are determined by comparing the volume occupied by the latex particles after having been compacted from a diluted dispersion in a centrifuge, relative to the volume of non-void particles in the same composition.

The hollow latex particles according to the invention may be obtained from particles comprising at least one polymer for the core and at least one polymer for the shell. The core polymer and the shell polymer may be obtained from a single polymerization step or from a sequence of polymerization steps.

The hollow latex particles according to the invention may be prepared by the conventional techniques of emulsion polymerization. Such processes are described especially in U.S. Pat. Nos. 4,427,836, 4,469,825, 4,594,363, 4,677,003, 4,920,160 and 4,970,241 or by the conventional techniques of polymerization that are described in EP-267,726, EP-331,421, U.S. Pat. Nos. 490,229 and 5,157,084.

The monomers employed for the shell of the latex particles are preferably constituted of one or more unsaturated non-ionic ethylenic units. Optionally, one or more monoethylenically unsaturated monomers containing at least one carboxylic acid group may be polymerized in the shell.

The monomers constituting the shell are selected such that they exhibit a glass transition temperature (Tg) which is sufficiently high to withstand the void of the hollow latex particle. Preferably, the glass transition temperature is greater than 50° C., more preferably greater than 60° C. and more preferably still greater than 70° C. This temperature Tg may be determined by DSC (differential scanning calorimetry).

The monomers employed in the emulsion polymerization in the core polymer of the latex particles of the invention are preferably constituted of one or more monoethylenically unsaturated monomers containing at least one carboxylic acid group. Preferably, the core comprises at least 5% by weight of monoethylenically unsaturated monomer containing at least one carboxylic acid group, relative to the total weight of the core monomers.

The core polymer may for example be obtained by emulsion homopolymerization of the monoethylenically unsaturated monomer containing at least one acid group or by copolymerization of two or three monoethylenically unsaturated monomers containing at least one acid group. Preferably, the monoethylenically unsaturated monomer containing at least one acid group is copolymerized with one or more ethylenically unsaturated nonionic monomers.

The core polymer or the shell polymer may contain from 0.1% to 20% by weight, preferably from 0.1% to 3% by weight, of polyethylenically unsaturated monomers such as ethylene glycol di(meth)acrylate, allyl(meth)acrylate, 1,3-butanediol di(meth)acrylate, diethylene glycol di(meth)acrylate, trimethylolpropane tri(meth)acrylate or divinylbenzene, relative to the total weight of core monomers. Alternatively the core polymer or the shell polymer may optionally contain from 0.1% to 60% by weight of butadiene, relative to the total weight of core monomers.

The monoethylenically unsaturated monomers containing at least one carboxylic acid group include, for example:

acrylic acid, methacrylic acid, acryloyloxypropionic acid, (meth)acryloyloxypropionic acid, itaconic acid, aconitic acid, maleic acid or maleic anhydride, fumaric acid, crotonic acid, monomethyl maleate, monomethyl fumarate and monomethyl itaconate.

More particularly exemplary is a monomer selected from acrylic acid and methacrylic acid.

The monoethylenically unsaturated nonionic monomers include, for example:

styrene, vinyltoluene, vinyl acetate, vinyl chloride, vinylidene chloride, acrylonitrile, (meth)acrylamide, $C_1$-$C_{20}$ alkyl esters of (meth)acrylic acid and ($C_3$-$C_{20}$) alkenyl esters of (meth)acrylic acid, such as methyl(meth)acrylate, ethyl (meth)acrylate, butyl(meth)acrylate, 2-ethylhexyl(meth) acrylate, benzyl(meth)acrylate, lauryl(meth)acrylate, oleyl (meth)acrylate, palmityl (meth)acrylate and stearyl(meth) acrylate. According to the invention, the term (meth)acrylic will denote the general expression encompassing both methacrylic or acrylic. The term (meth)acrylate will denote the general expression encompassing both methacrylate or acrylate.

The void part of the core of the latex particles is preferably produced by swelling the core with a swelling agent comprising one or more volatile compounds. The agent penetrates the shell in order to swell the core. The volatile components of the swelling agent may be subsequently removed by drying the latex particles, thus creating a void within the said particles. The agent is preferably an aqueous base. Exemplary are ammonia, ammonium hydroxide, alkali metal hydroxides such as sodium hydroxide and volatile amines such as trimethylamine or triethylamine.

The hollow latex particles may be introduced into the compositions of the invention with the swelling agent. In that case the volatile compounds are removed when the composition is dried. The hollow latex particles may also be added to the composition after the volatile compounds of the swelling agent have been removed.

The hollow latex particles which can be employed according to the invention are those described in U.S. Pat. No. 5,663,213 and EP-1-092,421.

According to one particular embodiment of the invention, the hollow latex particles employed will be those constituted of a copolymer of styrene and (meth)acrylic acid or one of its $C_1$-$C_{20}$ alkyl esters under the INCI name Styrene/Acrylates Copolymer, such as the product marketed under the trademark Sunspheres Powder by Rohm & Haas, which is an aqueous dispersion containing 86% of Styrene/Acrylates Copolymer in a mixture of 11% of PEG-8 Laurate, 2.5% of water and 0.5% of Sodium Dodecylbenzenesulfonate.

The hollow latex particles in accordance with the invention are preferably present in the compositions of the invention in amounts ranging from 0.1% to 20% by weight and more preferably from 0.5% to 10% by weight relative to the total weight of the composition.

Organic UV Screening Agents (or Sunscreen Agents):

The compositions of the invention comprise at least one mineral UV screening agent and/or at least one organic UV screening agent.

The organic UV screening agents are selected from water-soluble organic screening agents, fat-soluble organic screening agents or agents which are insoluble in the solvents presently included in suntan products, and mixtures thereof.

The organic UV screening agents are especially selected from cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives, especially those cited in U.S. Pat. No. 5,624,663; benzimidazole derivatives; imidazolines; bis-benzazolyl derivatives such as those described in EP-669,323 and U.S. Pat. No. 2,463,264; p-aminobenzoic acid (PABA) derivatives; methylenebis(hydroxyphenylbenzotriazole) derivatives such as those described in U.S. Pat. Nos. 5,237,071, 5,166,355, GB2303549, DE19726184 and EP-893,119; benzoxazole derivatives such as those described in EP-O-832,642, EP-1-027,883, EP-1-300,137 and DE10162844; screening polymers and screening silicones such as those described especially in WO 93/04665; α-alkylstyrene-derived dimers such as those described in DE19855649; 4,4-diarylbutadienes such as those described in EP-0-967,200, DE19746654, DE19755649, EP-A-1-008,586, EP-1-133,980 and EP-133,981; merocyanin derivatives such as those described in WO 04/006878, WO 05/058269 and WO 06/032741; and mixtures thereof.

Examples of complementary organic photoprotective agents include those denoted hereinbelow under their INCI name:

Cinnamic Derivatives:
Ethylhexyl Methoxycinnamate marketed in particular under the trademark "Parsol MCX" by Hoffmann LaRoche,
Isopropyl Methoxycinnamate,
Isoamyl Methoxycinnamate marketed under the trademark "Neo Heliopan E 1000" by Haarmann and Reimer,
DEA Methoxycinnamate,
Diisopropyl Methylcinnamate,
Glyceryl Ethylhexanoate Dimethoxycinnamate.
  Dibenzoylmethane Derivatives:
Butyl Methoxydibenzoylmethane marketed especially under the trademark "Parsol 1789" by Hoffmann LaRoche,
Isopropyl Dibenzoylmethane.
  para-Aminobenzoic Acid Derivatives:
PABA,
Ethyl PABA,
Ethyl Dihydroxypropyl PABA,
Ethylhexyl Dimethyl PABA marketed in particular under the trademark "Escalol 507" by ISP,
Glyceryl PABA,
PEG-25 PABA marketed under the trademark "Uvinul P25" by BASF.
  Salicylic Derivatives:
Homosalate marketed under the trademark "Eusolex HMS" by Rona/EM Industries,
Ethylhexyl Salicylate marketed under the trademark "Neo Heliopan OS" by Haarmann and Reimer,
Dipropylene Glycol Salicylate marketed under the trademark "Dipsal" by Scher,
TEA Salicylate marketed under the trademark "Neo Heliopan TS" by Haarmann and Reimer.
  β,β-Diphenylacrylate Derivatives:
Octocrylene marketed in particular under the trademark "Uvinul N539" by BASF,
Etocrylene marketed in particular under the trademark "Uvinul N35" by BASF.
  Benzophenone Derivatives:
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "Spectra-Sorb UV-24" by American Cyanamid,
Benzophenone-9 marketed under the trademark "Uvinul DS-49" by BASF, Benzophenone-12,
n-Hexyl 2-(4-diethylamino-2-hydroxybenzoyl)benzoate marketed under the trademark "Uvinul A+" by BASF.
  Benzylidenecamphor Derivatives:
3-Benzylidenecamphor manufactured under the trademark "Mexoryl SD" by Chimex,
4-Methylbenzylidenecamphor marketed under the trademark "Eusolex 6300" by Merck,
Benzylidene Camphor Sulfonic acid manufactured under the trademark "Mexoryl SL" by Chimex,
Camphor Benzalkonium Methosulfate manufactured under the trademark "Mexoryl SO" by Chimex,
Terephthalylidene Dicamphor Sulfonic acid manufactured under the trademark "Mexoryl SX" by Chimex,
Polyacrylamidomethyl Benzylidene Camphor manufactured under the trademark "Mexoryl SW" by Chimex.
  Phenylbenzimidazole Derivatives:
Phenylbenzimidazole Sulfonic acid marketed in particular under the trademark "Eusolex 232" by Merck,
Disodium Phenyl Dibenzimidazole Tetrasulfonate marketed under the trademark "Neo Heliopan AP" by Haarmann and Reimer.
  Phenylbenzotriazole Derivatives:
Drometrizole Trisiloxane marketed under the trademark "Silatrizole" by Rhodia Chimie,
Methylene bis(Benzotriazolyl) Tetramethylbutylphenol marketed in solid form under the trademark "MIXXIM BB/100" by Fairmount Chemical, or in micronized form as an aqueous dispersion under the trademark "Tinosorb M" by Ciba Specialty Chemicals.
  Triazine Derivatives:
bis-Ethylhexyloxyphenol Methoxyphenyl Triazine marketed under the trademark "Tinosorb S" by Ciba Geigy,
Ethylhexyl Triazone marketed in particular under the trademark "Uvinul T150" by BASF,
Diethylhexyl Butamido Triazone marketed under the trademark "Uvasorb HEB" by Sigma 3V,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
the symmetrical triazine screening agents described in U.S. Pat. No. 6,225,467, WO 2004/085412 (see compounds 6 and 9) or "Symmetrical Triazine Derivatives" IP.COM Journal, IP.COM Inc., West Henrietta, N.Y., US (20 Sep. 2004), especially 2,4,6-tris(biphenyl-1,3,5-triazines (in particular 2,4,6-tris(biphenyl-4-yl)-1,3,5-triazine and 2,4,6-tris(terphenyl)-1,3,5-triazine, which is found in the WO 06/035000, WO 06/034982, WO 06/034991, WO 06/035007, WO 2006/034992 and WO 2006/034985.

Anthranilic Derivatives:
Menthyl anthranilate marketed under the trademark "Neo Heliopan MA" by Haarmann and Reimer.
Imidazoline Derivatives:
Ethylhexyl Dimethoxybenzylidene Dioxoimidazoline Propionate.
Benzalmalonate Derivatives:
Polyorganosiloxane containing benzalmalonate functions, for instance Polysilicone-15, marketed under the trademark "Parsol SLX" by Hoffmann LaRoche.
4,4-Diarylbutadiene Derivatives:
1,1-Dicarboxy(2,2'-dimethylpropyl)-4,4-diphenylbutadiene.
Benzoxazole derivatives:
2,4-Bis[5-(1-dimethylpropyl)benzoxazol-2-yl(4-phenyl) imino]-6-(2-ethylhexyl)imino-1,3,5-triazine marketed under the trademark Uvasorb $K_2A$ by Sigma 3V,
and mixtures thereof.

The preferred organic screening agents are selected from:
Ethylhexyl Methoxycinnamate,
Ethylhexyl Salicylate,
Homosalate,
Butyl Methoxydibenzoylmethane,
Octocrylene,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulfonic Acid,
Disodium Phenyl Dibenzimidazole Tetrasulfonate,
Methylene bis-Benzotriazolyl Tetramethylbutylphenol,
Bis-Ethylhexyloxyphenol Methoxyphenyl Triazine,
Ethylhexyl Triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole Trisiloxane,
Polysilicone-15,
1,1-Dicarboxy(2,2'-dimethylpropyl)-4,4-diphenylbutadiene,
2,4-Bis[5-1-(dimethylpropyl)benzoxazol-2-yl(4-phenyl) imino]-6-(2-ethylhexyl)-imino-1,3,5-triazine,
and mixtures thereof.

The organic screening agents in accordance with the invention represent in general from 0.1% to 30%, preferably from 1% to 25%, of the total weight of the composition.

The inorganic UV screening agents in accordance with the present invention are metal oxide pigments. More preferentially, the inorganic screening agents of the invention are metal oxide particles having an average elementary particle size of less than or equal to 500 nm, more preferably from 5 nm to 500 nm and more preferably still from 10 nm to 100 nm, and preferentially from 15 to 50 nm.

They may be selected especially from titanium oxides, zinc oxides, iron oxides, zirconium oxides, cerium oxides or mixtures thereof.

Coated or uncoated metal oxide pigments of this kind are described more particularly in EP-A-0-518,773. Commercial pigments that may be mentioned include the products marketed by the companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

The coated pigments are more particularly titanium oxides that have been coated:
with silica, such as the product "Sunveil" by Ikeda,
with silica and iron oxide, such as the product "Sunveil F" by Ikeda,
with silica and alumina, such as the products "Microtitanium Dioxide MT 500 SA" and "Microtitanium Dioxide MT 100 SA" by Tayca and "Tioveil" by Tioxide,
with alumina, such as the products "Tipaque TTO-55 (B)" and "Tipaque TTO-55 (A)" by Ishihara and "UVT 14/4" by Kemira,
with alumina and aluminum stearate, such as the products "Microtitanium Dioxide MT 100 T, MT 100 TX, MT 100 Z and MT-01 by Tayca, the products "Solaveil CT-10 W" and "Solaveil CT 100" by Uniqema and the product "Eusolex T-AVO" by Merck,
with silica, alumina and alginic acid, such as the product "MT-100 AQ" by Tayca,
with alumina and aluminum laurate, such as the product "Microtitanium Dioxide MT 100 S" by Tayca,
with iron oxide and iron stearate, such as the product "Microtitanium Dioxide MT 100 F" by Tayca,
with zinc oxide and zinc stearate, such as the product "BR 351" by Tayca,
with silica and alumina and treated with a silicone, such as the products "Microtitanium Dioxide MT 600 SAS", "Microtitanium Dioxide MT 500 SAS" or "Microtitanium Dioxide MT 100 SAS" by Tayca,
with silica, alumina and aluminum stearate and treated with a silicone, such as the product "STT-30-DS" by Titan Kogyo,
with silica and treated with a silicone, such as the product "UV-Titan X 195" by Kemira,
with alumina and treated with a silicone, such as the products "Tipaque TTO-55 (S)" by Ishihara or "UV Titan M 262" by Kemira,
with triethanolamine, such as the product "STT-65-S" by Titan Kogyo,
with stearic acid, such as the product "Tipaque TTO-55 (C)" by Ishihara,
with sodium hexametaphosphate, such as the product "Microtitanium Dioxide MT 150 W" by Tayca,
$TiO_2$ treated with octyltrimethylsilane and marketed under the trademark "T 805" by Degussa Silices,
$TiO_2$ treated with polydimethylsiloxane and marketed under the trademark "70250 Cardre UF TiO2SI3" by Cardre,
anatase/rutile $TiO_2$ treated with a polydimethylhydrogenosiloxane and marketed under the trademark "Microtitanium Dioxide USP Grade Hydrophobic" by Color Techniques.

The uncoated titanium oxide pigments are marketed, for example, by Tayca under the trademarks "Microtitanium Dioxide MT 500 B" or "Microtitanium Dioxide MT 600 B", by Degussa under the trademark "P 25", by Wackher under the trademark "Transparent titanium oxide PW", by Miyoshi Kasei under the trademark "UFTR", by Tomen under the trademark "ITS" and by Tioxide under the trademark "Tioveil AQ".

The uncoated zinc oxide pigments are, for example:
those marketed under the trademark "Z-Cote" by Sunsmart;
those marketed under the trademark "Nanox" by Elementis;
those marketed under the trademark "Nanogard WCD 2025" by Nanophase Technologies.

The coated zinc oxide pigments are, for example:
those marketed under the trademark "Zinc Oxide CS-5" by Toshibi (ZnO coated with polymethylhydrogensiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in cyclopolymethylsiloxane/oxyethylenated polydimethylsiloxane, containing 30% or 50% of nanozinc oxides coated with silica and polymethylhydrogensiloxane);
those marketed under the trademark "NFD Ultrafine ZnO" by Daikin (ZnO coated with perfluoroalkyl phosphate and copolymer based on perfluoroalkylethyl as a dispersion in cyclopentasiloxane);
those marketed under the trademark "SPD-Z1" by Shin-Etsu (ZnO coated with silicone-grafted acrylic polymer, dispersed in cyclodimethylsiloxane);
those marketed under the trademark "Escalol Z100" by ISP (alumina-treated ZnO dispersed in an ethylhexyl methoxycinnamate/PVP-hexadecene/methicone copolymer mixture);
those marketed under the trademark "Fuji ZnO-SMS-10" by Fuji Pigment (ZnO coated with silica and polymethylsilsesquioxane);
those marketed under the trademark "Nanox Gel TN" by Elementis (ZnO dispersed at a concentration of 55% in $C_{12}$-$C_{15}$ alkyl benzoate with hydroxystearic acid polycondensate).

The uncoated cerium oxide pigments may be for example those marketed under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ" and "Nanogard WCD 2006 (FE 45R)" or by Mitsubishi under the trademark "TY-220".

The coated iron oxide pigments are marketed, for example, by Arnaud under the trademarks "Nanogard WCD 2008 (FE 45B FN)", "Nanogard WCD 2009 (FE 45B 556)", "Nanogard FE 45 BL 345" and "Nanogard FE 45 BL" or by BASF under the trademark "Transparent Iron Oxide".

Also exemplary are mixtures of metal oxides, especially of titanium dioxide and of cerium dioxide, including the equalweight mixture of silica-coated titanium dioxide and cerium dioxide, marketed by Ikeda under the trademark "Sunveil A", and also the mixture of alumina-, silica- and silicone-coated titanium dioxide and of zinc dioxide, such as the product "M 261" marketed by Kemira, or the mixture of alumina, silica- and glycerol-coated titanium dioxide and zinc dioxide, such as the product "M 211" marketed by Kemira.

According to the invention, particular preference is given to coated or uncoated titanium oxide pigments.

The inorganic screening agents in accordance with the invention represent generally from 0.5% to 40%, preferably from 1% to 30%, of the total weight of the composition.

The aqueous compositions of the invention may take any forms that are generally used for topical application, especially the forms of an oil-in-water emulsion (direct emulsion), water-in-oil emulsion (inverse emulsion) or else an aqueous gel.

The compositions of the invention may comprise all of the additives that are commonly included in cosmetics, and will find application in the Care, Makeup and Suntan product areas.

The aqueous compositions in accordance with the present invention may further comprise conventional cosmetic adjuvants especially selected from fatty substances, organic solvents, ionic or nonionic, hydrophilic or lipophilic thickeners, demulcents, humectants, opacifiers, stabilizers, emollients, silicones, antifoams, fragrances, preservatives, anionic, cationic, nonionic, zwitterionic or amphoteric surfactants, actives, fillers, polymers, propellants and alkalifying or acidifying agents, or any other ingredient commonly used in cosmetology and/or dermatology.

The fatty substances may be constituted of an oil or a wax or mixtures thereof. An oil is a compound that is liquid at ambient temperature. A wax is a compound that is solid or substantially solid at ambient temperature and whose melting point is generally greater than 35° C.

Oils that are exemplary include mineral oils (paraffin); plant oils (sweet almond oil, *macadamia* oil, grapeseed oil or jojoba oil); synthetic oils, for instance perhydrosqualene, fatty alcohols or fatty amides (for instance isopropyl lauroyl sarcosinate marketed under the trademark "Eldew SL-205" by Ajinomoto), fatty acids or fatty esters (for instance the $C_{12}$-$C_{15}$ alkyl benzoate marketed under the trademark "Finsolv TN" or "Witconol TN" by Witco, phenylethyl benzoate marketed under the trademark XTEND 226 by ISP or Spectrasol PEB by CP Hall, octyl palmitate, isopropyl lanolate and triglycerides, including capric/caprylic acid triglycerides, and dicaprylyl carbonate marketed under the trademark "Cetiol CC" by Cognis), oxyethylenated or oxypropylenated fatty esters and ethers; silicone oils (cyclomethicone and polydimethylsiloxanes, or PDMS) or fluoro oils, and polyalkylenes.

Waxy compounds that are exemplary include paraffin, carnauba wax, beeswax and hydrogenated castor oil.

Among the organic solvents that are exemplary are lower alcohols and polyols. These polyols may be selected from glycols and glycol ethers, for instance ethylene glycol, propylene glycol, butylene glycol, dipropylene glycol or diethylene glycol.

Hydrophilic thickeners that are exemplary include carboxyvinyl polymers such as the Carbopol products (carbomers) and the Pemulen products (acrylate/C10-C30-alkylacrylate copolymer); polyacrylamides, for instance the crosslinked copolymers marketed under the trademarks Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark "Hostacerin AMPS" (CTFA name: ammonium polyacryldimethyltauramide), cellulosic derivatives such as hydroxyethylcellulose; polysaccharides and especially gums such as xanthan gum; and mixtures thereof.

Lipophilic thickeners that are exemplary include synthetic polymers such as the poly $C_{10}$-$C_{30}$ alkyl acrylate marketed under the trademark "Doresco IPA 13-1" by Landec, or else modified clays such as hectorite and its derivatives, for instance the products marketed under the Bentone names.

As will be appreciated, one skilled in this art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be formulated according to techniques that are well known to those skilled in the art. They may be in particular in the form of a simple or complex emulsion (O/W, W/O, O/W/O or W/O/W) such as a cream, a milk or a cream-gel; in the form of an aqueous gel; in the form of a lotion, or a stick. They may optionally be packaged as an aerosol and may be in the form of a mousse or a spray.

The compositions according to the invention are preferably in the form of an oil-in-water or water-in-oil emulsion.

The emulsions generally contain at least one emulsifier selected from amphoteric, anionic, cationic and nonionic emulsifiers, which are used alone or as a mixture. The emulsifiers are appropriately selected according to the emulsion to be obtained (W/O or O/W).

As emulsifying surfactants that may be used for the preparation of the W/O emulsions, examples thereof include sorbitan, glycerol or sugar alkyl esters or ethers; silicone surfactants, for instance dimethicone copolyols, such as the mixture of cyclomethicone and of dimethicone copolyol, marketed under the trademark "DC 5225 C" by Dow Corning, and alkyldimethicone copolyols such as laurylmethicone copolyol marketed under the trademark "Dow Corning 5200 Formulation Aid" by Dow Corning; cetyldimethicone copolyol, such as the product marketed under the trademark Abil EM 90R by Goldschmidt, and the mixture of cetyldimethicone copolyol, of polyglyceryl isostearate (4 mol) and of hexyl laurate, marketed under the trademark Abil WE 09 by Goldschmidt. One or more co-emulsifiers may also be added thereto, which may be selected advantageously from the group comprising polyol alkyl esters.

Polyol alkyl esters that are especially exemplary include polyethylene glycol esters, for instance PEG-30 dipolyhydroxystearate, such as the product marketed under the trademark Arlacel P135 by ICI.

Glycerol and/or sorbitan esters that are especially exemplary include, for example, polyglyceryl isostearate, such as the product marketed under the trademark Isolan GI 34 by Goldschmidt, sorbitan isostearate, such as the product marketed under the trademark Arlacel 987 by ICI, sorbitan glyceryl isostearate, such as the product marketed under the trademark Arlacel 986 by ICI, and mixtures thereof.

For the O/W emulsions, examples of emulsifiers include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate marketed, for example, by ICI under the trademark Arlacel 165; oxyalkylenated (oxy)ethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the trademark Montanov 68 by SEPPIC, under the trademark Tegocare CG90 by Goldschmidt and under the trademark Emulgade KE3302 by Henkel, and also arachidyl glucoside, for example in the form of a mixture of arachidyl alcohol, behenyl alcohol and arachidyl glucoside, marketed under the trademark Montanov 202 by SEPPIC. According to one particular embodiment of the invention, the mixture of the alkylpolyglucoside as described above with the corresponding fatty alcohol may be in the form of a self-emulsifying composition as described, for example, in WO-A-92/06778.

When it is an emulsion, the aqueous phase of this emulsion may comprise a nonionic vesicular dispersion prepared according to known processes (Bangham, Standish and Watkins, *J. Mol. Biol.*, 13, 238 (1965), FR2315991 and FR2416008).

The compositions according to the invention find application in a large number of treatments, especially cosmetic treatments, of the skin, the lips and the hair, including the scalp, especially for protecting and/or caring for the skin, the lips and/or the hair, and/or for making up the skin and/or the lips.

The present invention also features the use of the compositions according to the invention as described above for the manufacture of products for cosmetically treating the skin, lips, nails, hair, eyelashes, eyebrows and/or scalp, especially care products, antisun products and makeup products.

The cosmetic compositions according to the invention may, for example, be used as care products and/or sun protection products for the face and/or body, of liquid to semi-liquid consistency, such as lotions, milks, creams of thicker or thinner consistency, gels and cream-gels. They may optionally be packaged as an aerosol and take the form of a foam or spray.

The cosmetic compositions according to the invention may be used, for example, as makeup products.

The compositions according to the invention in vaporizable fluid lotion form in accordance with the invention are applied to the skin or the hair in the form of fine particles by means of pressurization devices. The devices in accordance with the invention are well known to those skilled in the art and comprise non-aerosol pumps or atomizers, aerosol containers comprising a propellant, and also aerosol pumps using compressed air as propellant. These pumps are described in U.S. Pat. Nos. 4,077,441 and 4,850,517 (which form an integral part of the content of the description).

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The compositions according to the invention may also, further, comprise additional cosmetic and dermatological actives.

The additional actives may especially be selected from moisturizers, desquamating agents, agents improving the barrier function, depigmenting agents, antioxidants, dermo-decontracting agents, anti-glycation agents, agents stimulating the synthesis of dermal and/or epidermal macromolecules and/or preventing their degradation, agents stimulating fibroblast or keratinocyte proliferation and/or keratinocyte differentiation, agents promoting the maturation of the horny envelope, NO synthase inhibitors, peripheral benzodiazepine receptor (PBR) antagonists, agents increasing the activity of the sebaceous gland, agents stimulating the energy metabolism of cells, tensioning agents, fat restructuring agents, slimming agents, agents promoting the cutaneous microcirculation, calmatives and/or anti-irritants, sebo-regulating or anti-seborrheic agents, astringents, cicatrizing agents, anti-inflammatory agents and anti-acne agents.

One skilled in this art will select the said active or actives as a function of the effect which is desired on the skin, hair, eyelashes, eyebrows or nails, whether regime or regimen.

For caring for and/or making up skin which has aged, he or she will preferably select at least one active selected from moisturizers, desquamating agents, agents improving the barrier function, depigmenting agents, antioxidants, dermo-decontracting agents, anti-glycation agents, agents stimulating the synthesis of dermal and/or epidermal macromolecules and/or preventing their degradation, agents stimulating fibroblast or keratinocyte proliferation and/or keratinocyte differentiation, agents promoting the maturation of the horny envelope, NO synthase inhibitors, peripheral benzodiazepine receptor (PBR) antagonists, agents increasing the activity of the sebaceous gland, agents stimulating the energy metabolism of cells, fat restructuring agents, and agents promoting the cutaneous microcirculation for the area around the eyes.

The composition may further comprise at least one ingredient such as soft-focus effect fillers or agents promoting the natural coloring of the skin, intended to complement the biological effect of these actives or to provide an immediate visual anti-age effect.

For caring for and/or making up greasy skin, one skilled in this art will preferably select at least one active selected from desquamating agents, sebo-regulating or anti-seborrheic agents and astringents.

The composition may further comprise at least one additional ingredient intended for complementing the biological effect of these actives or providing an immediate visual effect; especially exemplary are matting agents, soft-focus effect fillers, fluorescers, agents promoting the naturally pinkish coloring of the skin, and abrasive fillers or exfoliants.

Moisturizers or Humectants:

Moisturizers or humectants that are exemplary include glycerol and derivatives thereof, urea and derivatives thereof, especially Hydrovance® marketed by National Starch, lactic acid, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* marketed under the trademark Moist 24® by Sederma, acrylic acid homopolymers, for instance Lipidure-HM® from NOF Corporation, beta-glucan and in particular sodium carboxymethyl beta-glucan from Mibelle-AG-Biochemistry; a mixture of passionflower oil, apricot oil, corn oil and rice bran oil marketed by Nestle under the trademark NutraLipids®; a C-glycoside derivative such as those described in WO 02/051828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB®; an oil of musk rose marketed by Nestlé; an extract of the microalga *Prophyridium cruentum* enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon; and arginine.

The moisturizer is preferably selected from urea and derivatives thereof, especially Hydrovance® marketed by National Starch, hyaluronic acid, AHAs, BHAs, acrylic acid homopolymers, for instance Lipidure-HM® from NOF Corporation, beta-glucan and in particular sodium carboxymethyl beta-glucan from Mibelle-AG-Biochemistry; a mixture of passionflower oil, apricot oil, corn oil and rice bran oil marketed by Nestle under the trademark NutraLipids®; a C-glycoside derivative such as those described in WO 02/051828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB); an oil of musk rose marketed by Nestlé; an extract of the microalga *Prophyridium cruentum* enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon; and arginine.

Desquamating Agents:

The term "desquamating agent" means any compound capable of acting:

either directly on desquamation by promoting exfoliation, such as β-hydroxy acids (BHA), in particular salicylic acid and derivatives thereof (including 5-n-octanoylsalicylic acid, also known as capryloyl salicylic acid as the INCI name); α-hydroxy acids (AHA), such as glycolic acid, citric acid, lactic acid, tartaric acid, malic acid or mandelic acid; 8-hexadecene-1,16-dicarboxylic acid or 9-octadecenedioic acid; urea and derivatives thereof; gentisic acid and derivatives thereof; oligofucoses; cinnamic acid; *Saphora japonica* extract; resveratrol, and certain jasmonic acid derivatives;

or on the enzymes involved in the desquamation or degradation of corneodesmosomes, glycosidases, stratum corneum chymotryptic enzyme (SCCE) or other proteases (trypsin, chymotrypsin-like). Exemplary are aminosulfonic compounds and in particular 4-(2-hydroxyethyl)piperazine-1-propanesulfonic acid (HEPES); 2-oxothiazolidine-4-carboxylic acid (procysteine) and derivatives thereof; derivatives of α-amino acids of glycine type (as described in EP-0-852,949, and also sodium methyl glycine diacetate marketed by BASF under the trademark Trilon M); honey; sugar derivatives such as O-octanoyl-6-D-maltose and N-acetylglucosamine.

As other desquamating agents that may be included in the composition according to the invention, exemplary are:

oligofructoses, EDTA and derivatives thereof, laminaria extracts, o-linoleyl-6D-glucose, (3-hydroxy-2-pentyl-cyclopentyl)acetic acid, glycerol trilactate, O-octanyl-6'-D-maltose, S-carboxymethylcysteine, siliceous derivatives of salicylate such as those described in EP-O-796,861, oligofucases such as those described in EP-O-218,200,5-acyl salicylic acid salts, actives with effects on transglutaminase, as in EP-O-899,330, extract of the flowers of ficus *Opuntia indica* such as Exfolactive® from Silab, 8-hexadecene-1,16-dicarboxylic acid, esters of glucose and of vitamin F, and mixtures thereof.

Preferred desquamating agents include β-hydroxy acids such as 5-n-octanoyl salicylic acid; urea; glycolic acid, citric acid, lactic acid, tartaric acid, malic acid or mandelic acid; 4-(2-hydroxyethyl)piperazine-1-propanesulfonic acid (HEPES); extract of *Saphora japonica*; honey; N-acetyl glucosamine; sodium methyl glycine diacetate, and mixtures thereof.

Even more preferentially, a desquamating agent selected from 5-n-octanoyl salicylic acid; urea; 4-(2-hydroxyethyl) piperazine-1-propanesulfonic acid (HEPES); extract of *Saphora japonica*; honey; N-acetyl glucosamine; sodium methyl glycine diacetate, and mixtures thereof, will be included in the compositions of the invention.

Agents for Improving the Barrier Function:

As agents for improving the barrier function, especially exemplary are arginine, serine, an extract of *Thermus thermophilus* such as Venuceane® from Sederma, an extract of the rhizome of wild yam (*Dioscorea villosa*) such as Actigen Y® from Active Organics, plankton extracts, for instance Omega Plankton® from Secma, yeast extracts, for instance Relipidium® from Coletica, a chestnut extract such as Recoverine® from Silab, a cedar bud extract such as Gatuline Zen® from Gattefosse, sphingosines, for instance salicyloyl sphingosine marketed under the trademark Phytosphingosine® SLC by Degussa, a mixture of xylitol, polyxylityl glycoside and xylitan, for instance Aquaxyl® from SEPPIC, extracts of Solanacea plants, for instance Lipidessence® from Coletica, omega 3 unsaturated oils such as oils of musk rose; and mixtures thereof.

Especially exemplary are ceramides or derivatives thereof, in particular ceramides of type 2 (for instance N-oleoyldihydrosphingosine), of type 3 (for instance stearoyl-4-hydroxysphinganine, as the INCI name) and of type 5 (for instance N-2-hydroxypalmitoyldihydrosphingosine, having the INCI name: hydroxypalmitoyl sphinganine), sphingoid-based compounds, glycosphingolipids, phospholipids, cholesterol and derivatives thereof, phytosterols, essential fatty acids, diacylglycerol, 4-chromanone and chromone derivatives, petroleum jelly, lanolin, shea butter, cocoa butter, lanolin and PCA salts.

As preferred agents having a restructuring effect on the cutaneous barrier, exemplary are an extract of *Thermus thermophilus*, an extract of wild yam rhizome (*Dioscorea villosa*), a yeast extract, a chestnut extract, a cedar bud extract, arginine, serine, ceramides especially of type 3 and 5; and mixtures thereof.

Serine, arginine or a mixture thereof will preferably be employed.

Depigmenting Agents:

Depigmenting agents that are especially exemplary include vitamin C and derivatives thereof and especially vitamin CG, CP and 3-O ethyl vitamin C, alpha and beta arbutin, ferulic acid, lucinol and derivatives thereof, kojic acid, resorcinol and derivatives thereof, tranexamic acid and derivatives thereof, gentisic acid, homogentisate, methyl gentisate or homogentisate, dioic acid, calcium D-pantheteine sulfonate, lipoic acid, ellagic acid, vitamin B3, linoleic acid and derivatives thereof, ceramides and homologues thereof, plant derivatives, for instance camomile, bearberry, the aloe family (vera, ferox, bardensis), mulberry or skullcap; a kiwi fruit (*Actinidia chinensis*) juice marketed by Gattefosse, an extract of *Paeonia suffruticosa* root, such as the product marketed by Ichimaru Pharcos under the trademark Botanpi Liquid B®, an extract of brown sugar (*Saccharum officinarum*), such as the molasses extract marketed by Taiyo Kagaku under the trademark Molasses Liquid, without this list being exhaustive.

As preferred depigmenting agents, exemplary are vitamin C and its derivatives and especially vitamin CG, vitamin CP and 3-O-ethyl-vitamin C, alpha- and beta-arbutin, ferulic acid, kojic acid, resorcinol and its derivatives, calcium D-pantetheine sulfonate, lipoic acid, ellagic acid, vitamin B3, a kiwi fruit juice (*Actinidia chinensis*) marketed by Gattefossé, an extract of *Paeonia suffruticosa* root such as that marketed by Ichimaru Pharcos under the trademark BOTANPI LIQUID B®.

Antioxidants:

Especially exemplary are tocopherol and esters thereof, in particular tocopherol acetate; ascorbic acid and derivatives thereof, in particular magnesium ascorbyl phosphate and ascorbyl glucoside; ferulic acid; serine; ellagic acid, phloretin, polyphenols, tannins, tannic acid, epigallocatechins and natural extracts containing them, anthocyans, rosemary extracts, olive leaf extracts, for instance those by Silab, green tea extracts, resveratrol and derivatives thereof, ergothioneine, N-acetylcysteine, an extract of the brown alga *Pelvetia canaliculata*, for instance Pelvetiane® from Secma, chlorogenic acid, biotin, chelating agents, such as BHT and BHA, N,N'-bis(3,4,5-trimethoxybenzyl)ethylenediamine and salts thereof; idebenone, plant extracts, for instance Pronalen Bioprotect™ by Provital; coenzyme Q10, bioflavonoids, SODs, phytantriol, lignans, melatonin, pidolates, glutathione, caprylyl glycol, phloretin, Totarol™ or extract of *Podocarpus totara* containing Totarol (totara-8,11,13-trienol or 2-phenanthrenol, 4b,5,6,7,8,8a,9,10-octahydro-4-b,8,8-trimethyl-1-(1-methylethyl)-; a jasmine extract such as the product marketed by Silab under the trademark Helisun®; hesperitin laurate such as Flavagrum PEG® by Engelhard Lyon; an extract of *Paeonia suffruticosa* root, such as the product marketed by Ichimaru Pharcos under the trademark Botanpi Liquid B® a lychee extract such as the lychee pericarp extract marketed by Cognis under the trademark Litchiderm LS 9704®, a pomegranate extract (*Punica granatum*), such as the product marketed by Draco Natural Products.

Other anti-aging agents that are exemplary include DHEA and derivatives thereof, boswellic acid, rosemary extracts, carotenoids (β-carotene, zeaxanthin and lutein), cysteic acid, copper derivatives and jasmonic acid.

Preferred antioxidants include ferulic acid; serine; phloretin, a pomegranate extract, biotin, chelating agents such as BHT, BHA, N,N'-bis(3,4,5-trimethoxybenzyl)ethylenediamine and salts thereof; caprylyl glycol, phloretin, Totarol™, a jasmine extract such as the product marketed by Silab under the trademark Helisun®; hesperitin laurate such as Flavagrum PEG® by Engelhard Lyon; an extract of *Paeonia suffruticosa* root, such as the product marketed by Ichimaru Pharcos under the trademark Botanpi Liquid B®.

Dermo-Relaxing or Dermo-Decontracting Agents:

Examples thereof include manganese gluconate and other salts, adenosine, alverine citrate and salts thereof, glycine, an extract of Iris pallida, a hexapeptide (Argeriline R from Lipotec) or sapogenins, for instance wild yam and the carbonyl amines described in EP-1-484,052. Examples of sapogenins include those described in WO 02/47650, in particular wild yam, the diosgenin extracted especially from *Dioscorea opposita* or any extract naturally containing or containing after treatment one or more sapogenins (wild yam rhizome, agave leaf, which contains hecogenin and tigogenin, extracts of Liliacea plants and more particularly yucca or smilax containing smilagenin and sarsapogenin, or sarsaparilla root) or Actigen Y by Actives Organics; or ginger.

Also exemplary are DMAE (dimethyl MEA), extracts of sea fennel, of rockrose, of *helichrysum*, of anise, of paracress, and an extract of *Acmella oleracea*, for instance Gatuline® from Gattefossé.

Preferred dermo-relaxing agents include adenosine, manganese gluconate, wild yam, sea fennel, glycine and alverine.

Anti-Glycation Agents:

The term "anti-glycation agent" means a compound that prevents and/or reduces the glycation of skin proteins, in particular dermal proteins such as collagen.

Anti-glycation agents that are exemplary include extracts of plants of the Ericacea family, such as an extract of blueberry (*Vaccinium angustifolium* or *Vaccinium myrtillus*), for example the product marketed under the trademark Blueberry Herbasol Extract PG by Cosmetochem, ergothioneine and derivatives thereof, hydroxystilbenes and derivatives thereof, such as resveratrol and 3,3',5,5'-tetrahydroxystilbene (these anti-glycation agents are described in FR 2,802,425, FR 2,810,548, FR 2,796,278 and FR 2,802,420, respectively), dihydroxystilbenes and derivatives thereof, polypeptides of arginine and of lysine such as the product marketed under the trademark Amadorine® by Solabia, carcinine hydrochloride (marketed by Exsymol under the trademark Alistin®), an extract of *Helianthus annuus*, for instance Antiglyskin® from Silab, wine extracts such as the extract of powdered white wine on a maltodextrin support marketed under the trademark Vin blanc déshydraté 2F by Givaudan, thioctic acid (or alpha-lipoic acid), a mixture of extract of bearberry and of marine glycogen, for instance Aglycal LS 8777® from Laboratoires Sérobiologiques, and an extract of black tea, for instance Kombuchka® from Sederma, and mixtures thereof.

Preferred anti-glycation agents include extracts of blueberry (*Vaccinium myrtillus*) and extract of black tea.

Agents for stimulating the synthesis of dermal and/or epidermal macromolecules and/or for preventing their degradation.

Among the active agents for stimulating the dermal macromolecules or for preventing their degradation, exemplary are those acting:

either on collagen synthesis, such as extracts of *Centella asiatica*, asiaticosides and derivatives thereof; ascorbic acid or vitamin C and derivatives thereof; synthetic peptides such as iamin, biopeptide CL or palmitoyl oligopeptide marketed by Sederma; peptides extracted from plants, such as the soybean hydrolysate marketed by Coletica under the trademark Phytokine®; rice peptides such as Nutripeptide® from Silab, methylsilanol mannuronate such as Algisium C® marketed by Exsymol; plant hormones such as auxins and lignans; folic acid; and an extract of *Medicago sativa* (alfalfa) such as the product marketed by Silab under the trademark Vitanol®; a peptide extract of hazelnut such as the product marketed by Solabia under the trademark Nuteline C®; and arginine;

or on the inhibition of collagen degradation, in particular agents acting on the inhibition of metalloproteases (MMP) more particularly such as MMP 1, 2, 3 and 9. Mention may be made of: retinoids and derivatives, extracts of *Medicago sativa* such as Vitanol® from Silab, an extract of *Aphanizomenon flos-aquae* (Cyanophyceae) marketed under the trademark Lanablue® by Atrium Biotechnologies, oligopeptides and lipopeptides, lipoamino acids, the malt extract marketed by Coletica under the trademark Collalift®; blueberry or rosemary extracts; lycopene; isoflavones, derivatives thereof or plant extracts containing them, in particular extracts of soybean (marketed, for example, by Ichimaru Pharcos under the trademark Flavosterone SB®), of red clover, of flax or of kakkon; an extract of lychee such as the lychee pericarp extract marketed by Cognis under the trademark Litchiderm LS 9704®; Dipalmitoyl Hydroxyproline marketed by SEPPIC under the trademark Sepilift DPHP®: Baccharis genistelloide or Baccharine marketed by Silab, an extract of moringa such as Arganyl LS 9781® from Cognis; the sage extract described in FR-A-2 812 544 from the Labiatae family (*Salvia officinal* ranges by Flacksmann), an extract of rhododendron, a blueberry extract, and an extract of *Vaccinium myrtillus* such as those described in FR-A-2 814 950;

or on the synthesis of molecules belonging to the elastin family (elastin and fibrillin), such as: retinol and derivatives, in particular retinol palmitate; the extract of *Saccharomyces cerevisiae* marketed by LSN under the trademark Cytovitin®); and the extract of the alga *Macrocystis pyrifera* marketed by Secma under the trademark Kelpadelie®; a peptide extract of hazelnut such as the product marketed by Solabia under the trademark Nuteline C®;

or on inhibition of elastin degradation, such as the peptide extract of seeds of *Pisum sativum* marketed by LSN under the trademark Parelastyl®; heparinoids; and the N-acylamino amide compounds described in WO 01/94381, such as {2-[acetyl(3-trifluoromethylphenyl)amino]-3-methylbutyrylamino}acetic acid, also known as N—[N-acetyl, N'-(3-trifluoromethyl)phenylvalyl] glycine, or N-acetyl-N-[3-(trifluoromethyl)phenyl]valyl glycine or acetyl trifluoromethyl phenyl valylglycine, or an ester thereof with a $C_1$-$C_6$ alcohol; an extract of rice peptides such as Colhibin® from Pentapharm, or an extract of *Phyllanthus emblica* such as Emblica® from Rona;

or on the synthesis of glycosaminoglycans, such as the product of fermentation of milk with *Lactobacillus vulgaris*, marketed by Brooks under the trademark Biomin Yoghurt®; the extract of the brown alga *Padina pavonica* marketed by Alban Müller under the trademark HSP3®; the *Saccharomyces cerevisiae* extract available especially by Silab under the trademark Firmalift® or by LSN under the trademark Cytovitin®; an extract of *Laminaria ochroleuca* such as Laminaine® from Secma; essence of Mamaku from Lucas Meyer, and an extract of cress (Odraline®D from Silab);

or on the synthesis of fibronectin, such as the extract of the zooplankton Salina marketed by Seporga under the trademark GP4G®; the yeast extract available especially by Alban Müller under the trademark Drieline®; and the palmitoyl pentapeptide marketed by Sederma under the trademark Matrixil®.

Among the active agents for stimulating epidermal macromolecules, such as fillagrin and keratins, especially exemplary are the extract of lupin marketed by Silab under the trademark Structurine®; the extract of *Fagus sylvatica* beech buds marketed by Gattefossé under the trademark Gatuline® RC; and the extract of the zooplankton Salina marketed by Seporga under the trademark GP4G®D; the copper tripeptide from Procyte; a peptide extract of *Voandzeia substerranea* such as the product marketed by Laboratoires Sérobiologiques under the trademark Filladyn LS 9397®.

Preferably, an active agent that stimulates the synthesis of dermal and/or epidermal macromolecules and/or that prevents their degradation, selected from agents for stimulating the synthesis of glycosaminoglycans, agents for inhibiting elastin degradation, agents for stimulating fibronectin synthesis, agents for stimulating the synthesis of epidermal macromolecules, and mixtures thereof, will be employed.

Even more preferentially, an active agent that stimulates the synthesis of the glycosaminoglycans, selected from an extract of the brown alga *Padina pavonica*, an extract of *Saccharomyces cerevisiae*, an extract of *Laminaria ochroleuca*, essence of Mamaku, and an extract of cress, and mixtures thereof, will even more preferentially be employed.

As preferred active agents for stimulating the synthesis of dermal and/or epidermal macromolecules and/or for preventing their degradation, exemplary are:

synthetic peptides such as iamin, the biopeptide CL or palmitoyloligopeptide marketed by Sederma; peptides extracted from plants, such as the soybean hydrolysate marketed by Coletica under the trademark Phytokine®;

rice peptides such as Nutripeptide® from Silab, methylsilanol mannuronate such as Algisium CO marketed by Exsymol; folic acid; an extract of *Medicago sativa* (alfalfa), such as the product marketed by Silab under the trademark Vitanol®; a peptide extract of hazelnut, such as the product marketed by Solabia under the trademark Nuteline C®; arginine; an extract of *Aphanizomenon flos-aquae* (Cyanophyceae) marketed under the trademark Lanablue® by Atrium Biotechnologies, the malt extract marketed by Coletica under the trademark Collalift®, lycopene; an extract of lychee; an extract of moringa such as Arganyl LS 9781® from Cognis; an extract of *Vaccinium myrtillus* such as those described in FR-A-2 814 950; retinol and derivatives thereof, in particular retinyl palmitate; the extract of *Saccharomyces cerevisiae* marketed by LSN under the trademark Cytovitin®; a peptide extract of hazelnut such as the product marketed by Solabia under the trademark Nuteline C®; {2-[acetyl(3-trifluoromethylphenyl)amino]-3-methylbutyrylamino}acetic acid, also known as N—[N-acetyl, N'-(3-trifluoromethyl)phenylvalyl]glycine, or N-acetyl-N-[3-(trifluoromethyl)phenyl]valylglycine or acetyl trifluoromethyl phenyl valylglycine, or an ester thereof with a $C_1$-$C_6$ alcohol; an extract of rice peptides such as Colhibin® from Pentapharm, or an extract of *Phyllanthus emblica* such as Emblica® from Rona; the extract of the brown alga *Padina pavonica* marketed by Alban Müller under the trademark HSP3®; the extract of *Saccharomyces cerevisiae* available especially by Silab under the trademark Firmalift® or by LSN under the trademark Cytovitin®; an extract of *Laminaria ochroleuca* such as Laminaine® from Secma; the essence of Mamaku from Lucas Meyer, the extract of lupin marketed by Silab under the trademark Structurine®; the extract of *Fagus sylvatica* beech buds marketed by Gattefossé under the trademark Gatuline® RC.

Agents for Stimulating Fibroblast or Keratinocyte Proliferation and/or Keratinocyte Differentiation:

The agents for stimulating fibroblast proliferation that may be included in the compositions according to the invention may be selected, for example, from plant proteins or polypeptides, extracted especially from soybean (for example a soybean extract marketed by LSN under the trademark Eleseryl SH-VEG 8® or marketed by Silab under the trademark Raffermine®); an extract of hydrolysed soybean proteins such as Ridulisse® from Silab; and plant hormones such as gibberellins and cytokinins; a peptide extract of hazelnut such as the product marketed by Solabia under the trademark Nuteline C®.

Preferably, an agent that promotes keratinocyte proliferation and/or differentiation will be employed.

The agents for stimulating keratinocyte proliferation that may be included in the compositions according to the invention especially comprise adenosine; phloroglucinol, the extract of *Hydrangea macrophylla* leaves, for instance Amacha Liquid E® from Ichimaru Pharcos, a yeast extract such as Stimoderm® from CLR; the extract of *Larrea divaricata* such as Capislow® from Sederma, mixtures of extracts of papaya, of olive leaves and of lemon, such as Xyleine® from Vincience, the extract of *Hydrangea macrophylla* leaves, for instance Amacha Liquid E® from Ichimaru Pharcos, retinol and esters thereof, including retinyl palmitate, phloroglucinol, the nut cake extracts marketed by the Gattefossé and the extracts of *Solanum tuberosum* such as Dermolectine® marketed by Sederma.

Among the agents for stimulating keratinocyte differentiation are, for example, minerals such as calcium; sea fennel, a peptide extract of lupin, such as the product marketed by Silab under the trademark Structurine®; sodium beta-sitosteryl sulfate, such as the product marketed by Seporga under the trademark Phytocohesine®; and a water-soluble extract of corn, such as the product marketed by Solabia under the trademark Phytovityl®; a peptide extract of *Voandzeia substerranea* such as the product marketed by Laboratoires Sérobiologiques under the trademark Filladyn LS 9397®; and lignans such as secoisolariciresinol, and retinol and esters thereof, including retinyl palmitate.

As agents for stimulating keratinocyte proliferation and/or differentiation, exemplary are the oestrogens such as oestradiol and homologues; cytokines.

As preferred active agents for stimulating fibroblast or keratinocyte proliferation and/or keratinocyte differentiation, exemplary are plant proteins or polypeptides, extracted especially from soybean (for example a soybean extract marketed by LSN under the trademark Eleseryl SH-VEG 8® or marketed by Silab under the trademark Raffermine®); an extract of hydrolysed soybean proteins such as Ridulisse® from Silab; a peptide extract of hazelnut such as the product marketed by Solabia under the trademark Nuteline C®; adenosine; phloroglucinol, a yeast extract such as Stimoderm® from CLR; a peptide extract of lupin such as the product marketed by Silab under the trademark Structurine®; a water-soluble corn extract, such as the product marketed by Solabia under the trademark Phytovityl®; a peptide extract of *Voandzeia substerranea*, such as the product marketed by Laboratoires Sérobiologiques under the trademark Filladyn LS 9397®D; retinol and esters thereof, including retinyl palmitate.

Agents for Promoting the Maturation of the Horny Envelope:

Agents that participate in the maturation of the horny envelope, which becomes impaired with age and induces a decrease in transglutaminase activity, may be included in the compositions of the invention. Examples are urea and derivatives thereof and in particular Hydrovance® from National Starch and the other active agents mentioned in L'Oréal FR 2 877 220 (unpublished).

NO-Synthase Inhibitors:

The agent with an inhibitory action on NO synthase may be selected from OPCs (procyannidol oligomers); plant extracts of the species *Vitis vinifera* marketed especially by Euromed under the trademark "Leucocyanidines de raisins extra", or by Indena under the trademark Leucoselect®, or finally by Hansen under the trademark "Extrait de marc de raisin"; plant extracts of the species *Olea europaea* preferably obtained from olive tree leaves and marketed especially by Vinyals in the form of a dry extract, or by Biologia & Technologia under the trademark Eurol® BT; and plant extracts of the species *Gingko biloba*, preferably a dry aqueous extract of this plant marketed by Beaufour under the trademark "Ginkgo biloba extrait standard", and mixtures thereof.

Peripheral Benzodiazepine Receptor (PBR) Antagonists:

Exemplary are 1-(2-chlorophenyl)-N-(1-methylpropyl)-3-isoquinoline carboxamide; the compounds described in WO 03/030 937 and WO 03/068 753, pyridazino[4,5-b]indole-1-acetamide derivatives of general formula (VII) as described in WO 00/44384.

Agents for Increasing the Activity of the Sebaceous Glands:

Exemplary are methyl dehydrojasmonate, hecogenin, hedione and O-linoleyl-6D-glucose, and mixtures thereof.

Agents for Stimulating the Energy Metabolism of Cells:

The active agent for stimulating the energy metabolism of cells may be selected, for example, from biotin, an extract of *Saccharomyces cerevisiae* such as Phosphovital® from Sederma, the mixture of sodium, manganese, zinc and magnesium salts of pyrrolidonecarboxylic acid, for instance Physiogenyl®D from Solabia, a mixture of zinc, copper and magnesium gluconate, such as Sepitonic M3® from SEPPIC, and mixtures thereof; a beta-glucan derived from *Saccharomyces cerevisiae*, such as the product marketed by Mibelle AG Biochemistry.

Tensioning Agents:

The term "tensioning agent" according to the invention means compounds having a tensioning effect, i.e., being able to make the skin taut.

According to the invention, the term "tensioning agent" generally means any compound that is soluble or dispersible in water at a temperature ranging from 25° C. to 50° C. at a concentration of 7% by weight in water or at the maximum concentration at which a medium of uniform appearance is formed and producing at this concentration of 7% or at this maximum concentration in water a shrinkage of more than 15% in the test described below.

The maximum concentration at which a medium of uniform appearance forms is determined to within ±10% to preferably to within ±5%.

The expression "medium of uniform appearance" means a medium that does not contain any aggregates that are visible to the naked eye.

For the determination of the said maximum concentration, the tensioning agent is gradually added to the water with deflocculating stirring at a temperature ranging from 25° C. to 50° C., and the mixture is then stirred for one hour. The mixture thus prepared is then examined after 24 hours to see if it is of uniform appearance (absence of aggregates visible to the naked eye).

The tensioning effect may be characterized by an in vitro shrinkage test.

A homogeneous mixture of the tensioning agent in water, at a concentration of 7% by weight or at the maximum concentration described above, is prepared beforehand and as described previously.

30 μl of the homogeneous mixture are placed on a rectangular sample (10×40 mm, thus having an initial width $L_0$ of 10 mm) of elastomer with a modulus of elasticity of 20 MPa and a thickness of 100 μm.

After drying for 3 hours at 22±3° C. and 40±10% relative humidity RH, the elastomer sample has a shrunken width, noted $L_{3h}$, due to the tension exerted by the applied tensioning agent.

The tensioning effect (TE) of the said polymer is then quantified in the following manner:

'TE'=$(L_0-L_{3h}/L_0)\times 100$ as % with $L_0$=initial width 10 mm and $L_{3h}$=width after 3 hours of drying The tensioning agent may be selected from:
plant or animal proteins and hydrolysates thereof;
polysaccharides of natural origin;
mixed silicates;
colloidal particles of mineral fillers;
synthetic polymers;
and mixtures thereof.

One skilled in this art will know how to choose, from the chemical categories listed above, the materials corresponding to the tensioning test as described above.

Especially exemplary are:
(a) plant proteins and protein hydrolysates, in particular of corn, rye, wheat, buckwheat, sesame, spelt, pea, bean, lentil, soybean and lupin,
(b) polysaccharides of natural origin, especially (a) polyholosides, for example (i) in the form of starch derived especially from rice, corn, potato, cassava, pea, wheat, oat, etc. or (ii) in the form of carrageenans, alginates, agars, gellans, cellulose polymers and pectins, advantageously as an aqueous dispersion of gel microparticles, and (b) latices consisting of shellac resin, sandarac gum, dammar resins, elemi gums, copal resins, cellulose derivatives, and mixtures thereof,
(c) mixed silicates, especially phyllosilicates and in particular Laponites,
(d) colloidal particles of mineral fillers with a number-average diameter of from 0.1 and 100 nm and preferably from 3 and 30 nm, and selected, for example, from: silica, silica-alumina composites, cerium oxide, zirconium oxide, alumina, calcium carbonate, barium sulfate, calcium sulfate, zinc oxide and titanium dioxide. As silica-alumina composite colloidal particles that may be included in the compositions according to the invention, examples include those marketed by Grace under the trademarks Ludox AM, Ludox AM-X 6021, Ludox HSA and Ludox TMA,
(e) synthetic polymers, such as polyurethane latices or acrylic-silicone latices, in particular those described in EP-1-038,519, such as a polydimethylsiloxane grafted with propylthio(polymethyl acrylate), propylthio(polymethyl methacrylate) and propylthio(polymethacrylic acid), or, alternatively, a polydimethylsiloxane grafted with propylthio(polyisobutyl methacrylate) and propylthio(polymethacrylic acid). Such grafted silicone polymers are especially marketed by 3M under the trademarks VS 80, VS 70 and LO21.

The tensioning agent will be present in the composition in an amount that is effective for obtaining the desired biological effect according to the invention.

By way of example, the tensioning agent may be included in the compositions according to the invention in a content ranging from 0.01% to 30% by weight of active material and preferably from 1% to 30% by weight of active material relative to the total weight of the composition.

The term "active material" is intended to exclude the medium in which the tensioning agent may be dissolved or dispersed in its commercial form, for example in the case of dispersions of colloidal particles.

It is also possible, especially for complementing and/or potentializing the effect of tensioning agents, to employ agents which increase the expression of mechanoreceptors, such as agents which increase the expression of integrins.

An example is a rye seed extract, such as that marketed by Silab under the trademark Coheliss®.

Fat Restructuring Agents:

"Fat restructuring agents" are, according to the invention, agents which are capable of stimulating lipogenesis and promoting adipocyte differentiation, thereby making it possible to prevent or slow down the wasting of the fats contained in the support tissues of the skin, as is also called 'wasting of the fat structure of the skin'.

'Fat structure of the skin' means the network of fat cells which form the volumes over which the facial skin rests and moulds itself to.

These agents are useful for lessening the loss of skin density and/or the wasting of the fat structure of the skin, more particularly on the cheeks and in the area around the eye, and/or for preventing the collapse and/or hollowing of the volumes of the face, the loss of consistency of the skin and/or its maintenance, more particularly on the cheeks and in the area around the eye, and/or for improving the underlying volumes of the skin of the face and/or neck, more particularly on the cheeks, of the oval of the face and of the area around the eye, and/or for improving the density, springiness and maintenance of the skin, more particularly on the cheeks, of the oval of the face and of the area around the eye, and/or of remodelling the features of the face, more particularly the oval of the face.

Examples of fat restructuring agents include, especially, a black tea extract, such as the extract of fermented black tea that is marketed by Sederma under the trademark Kombuchka®, and an extract of *Artemisia abrotanum*, such as that marketed by Silab under the trademark Pulpactyl®.

Slimming Agents:

Slimming (lipolytic) agents that are especially exemplary include caffeine, theophylline and its derivatives, theobromine, sericosine, asiatic acid, acefylline, aminophylline, chloroethyltheophylline, diprofylline, diniprophylline, etamiphylline and its derivatives, etofylline and proxyphylline; extracts of tea, of coffee, of guarana, of maté, of cola (*Cola nitida*) and especially the dry extract of guarana fruit (*Paulina sorbilis*) containing 8% to 10% caffeine; extracts of climbing ivy (*Hedera helix*), of arnica (*Arnica montana* L), of rosemary (*Rosmarinus officinalis* N), of marigold (*Calendula officinalis*), of sage (*Salvia officinalis* L), of ginseng (*Panax ginseng*), of St.-John's wort (*Hypericum perforatum*), of butcher's-broom (*Ruscus aculeatus* L), of meadowsweet (*Filipendula ulmaria* L), of orthosiphon (*Orthosiphon stamincus Benth*), of birch (*Betula alba*), of pumpwood and of argan tree, extracts of *ginkgo biloba*, extracts of horsetail, extracts of escin, extracts of cangzhu, extracts of *Chrysanthellum indicum*, extracts of diosgenin-rich Dioscorea plants or pure diosgenin or hecogenin and derivatives thereof, extracts of Ballota, extracts of *Guioa*, of *Davallia*, of *Terminalia*, of *Barringtonia*, of *Trema* or of *Antirobia*, the extract of bitter orange pips; an extract of husks of cocoa beans (*Theobroma cacao*) such as the product marketed by Solabia under the trademark Caobromine®.

Agents for Promoting the Cutaneous Microcirculation:

The active agent acting on the cutaneous microcirculation may be used for preventing dulling of the complexion and/or for improving the appearance of the area around the eye, especially for reducing shadows. It may be selected, for example, from an extract of maritime pine bark, for instance Pycnogenol® from Biolandes, manganese gluconate (Givobio GMn® from SEPPIC), an extract of *Ammi visnaga* such as Visnadine from Indena, extract of lupin (Eclaline® from Silab), the protein coupling of hydrolysed wheat/palmitic acid with palmitic acid, such as Epaline 100 from Laboratoires Carilène, the extract of bitter orange blossom (Remoduline® from Silab), vitamin P and derivatives thereof, for instance methyl-4 esculetol sodium monoethanoate marketed under the trademark Permethol® by Sephytal, extracts of Ruscus, of common horse chestnut, of ivy, of ginseng and of melilot, caffeine, nicotinate and derivatives thereof, lysine and derivatives thereof, for instance Asparlyne®D from Solabia, an extract of black tea such as Kombuchka from Sederma; rutin salts; an extract of the alga *Corallina officinalis*, such as the product marketed by Codif; and mixtures thereof.

As preferred agents for promoting the cutaneous microcirculation, exemplary are caffeine, an extract of bitter orange blossom, an extract of black tea, rutin salts and an extract of the alga *Corallina officinalis*.

Calmatives or Anti-Irritants:

The term "calmative" means a compound that reduces the sensation of stinging, itching or tautness of the skin.

As calmatives that may be included in the compositions according to the invention, exemplary are:

procyannidol oligomers, vitamins E, C, B5 and B3, caffeine and derivatives thereof, pentacylic triterpenes and plant extracts containing them, β-glycyrrhetinic acid and salts or derivatives thereof (stearyl glycyrrhetate, 3-stearoyloxyglycyrrhetic acid or glycyrrhetinic acid monoglucuronide) and also plants containing them (e.g., *Glycyrrhiza glabra*), oleanolic acid and salts thereof, ursolic acid and salts thereof, boswellic acid and salts thereof, betulinic acid and salts thereof, an extract of *Paeonia suffruticosa* and/or *lactiflora*, an extract of *Laminaria saccharina*, extracts of *Centella asiatica*, Canola oil, bisabolol, the phosphoric diester of vitamin E and C, for instance Sepivital EPC® from SEPPIC, camomile extracts, allantoin, omega-3 unsaturated oils such as musk rose oil, blackcurrant oil, Ecchium oil, fish oil or beauty-leaf oil, plankton extracts, capryloyl glycine, a mixture of water lily blossom extract and of palmitoylproline, such as the product marketed under the trademark Seppicalm VG® by SEPPIC, an extract of *Boswellia serrata*, an extract of *Centipeda cunninghami*, such as the product marketed under the trademark Cehami PF® by TRI-K Industries, an extract of sunflower seeds, in particular Hélioxine® from Silab, an extract of *Linum usitatissimum* seeds, for instance Sensiline® from Silab, tocotrienols, piperonal, an extract of *Epilobium angustifolium*, such as the product marketed under the trademark Canadian Willowherb Extract by Fytokem Products, Aloe vera, phytosterols, cornflower water, rose water, an extract of mint, in particular of mint leaves, for instance Calmiskin® from Silab, anise derivatives, filamentous bacteria, for instance *Vitreoscilla filiformis* as described in EP,761,204 and marketed by Chimex under the trademark Mexoryl SBG®, an extract of rose petals, for instance Rose Flower Herbasol® extract by Cosmetochem, shea butter, a mixture of the waxy fraction of barley seeds obtained by supercritical $CO_2$, of shea butter and of argan oil, for instance Stimu-tex AS®from Pentapharm, alkaline-earth metal salts, especially of strontium, a fermented extract of Alteromonas marketed under the trademark Abyssine® by Atrium Biotechnologies; spring water from the Vichy basin, such as waters originating from the Célestins, Chomel, Grande-Grille, Hopital, Lucas and Parc sources, and preferably water from the Lucas source; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Preferred calmatives according to the invention include:

β-glycyrrhetinic acid and salts or derivatives thereof (stearyl glycyrrhetate, 3-stearoyloxyglycyrrhetic acid or glycyrrhetinic acid monoglucuronide) and also plants containing them (e.g. *Glycyrrhiza glabra*); ursolic acid and salts thereof; extracts of *Centella asiatica*, Canola oil, bisabolol; camomile extracts, allantoin; a mixture of extract of water lily blossom and of palmitoylproline, such as the product marketed under the trademark Seppicalm VG® by SEPPIC; Aloe vera, rose water, extract of mint, in particular of mint leaves, such as Calmiskin® from Silab, filamentous bacteria such as *Vitreoscilla filiformis* as described in EP-761,204 and marketed by Chimex under the trademark Mexoryl SBG®, an extract of rose petals such as Rose Flower Herbasol® extract by Cosmetochem, shea butter, a fermented extract of Alteromonas marketed under the trademark Abyssine® by Atrium Biotechnologies; spring water from the Vichy basin, such as waters originating from the Celestins, Chomel, Grande-Grille, Hôpital, Lucas and Parc sources, and preferably water from the Lucas source; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Sebo-Regulating or Anti-Seborrhoeic Agents:

The term "sebo-regulating or anti-seborrhoeic agents" especially means agents capable of regulating the activity of the sebaceous glands.

Especially exemplary are:

retinoic acid, benzoyl peroxide, sulfur, vitamin B6 (or pyridoxine), selenium chloride and sea fennel;

mixtures of extract of cinnamon, of tea and of octanoyl-lycine such as Sepicontrol A5 TEA® from SEPPIC;

the mixture of cinnamon, sarcosine and octanoylglycine marketed especially by SEPPIC under the trademark Sepicontrol A5®;

zinc salts such as zinc gluconate, zinc pyrrolidonecarboxy-late (or zinc pidolate), zinc lactate, zinc aspartate, zinc carboxylate, zinc salicylate and zinc cysteate;

copper derivatives and in particular copper pidolate such as Cuivridone® from Solabia;

extracts of plants of the species *Arnica montana*, *Cinchona succirubra*, *Eugenia caryophyllata*, *Humulus lupulus*, *Hypericum perforatum*, *Mentha piperita*, *Rosmarinus officinalis*, *Salvia oficinalis* and *Thymus vulgaris*, all marketed, for example, by Maruzen;

extracts of meadowsweet (*Spiraea ulmaria*), such as the product marketed under the trademark Sebonormine® by Silab;

extracts of the alga *Laminaria saccharina*, such as the product marketed under the trademark Phloroginee by Biotechmarine;

mixtures of extracts of salad burnet root (*Sanguisorba officinalis/Poterium officinale*), of ginger rhizomes (*Zingiber officinalis*) and of cinnamon bark (*Cinnamomum cassia*), such as the product marketed under the trademark Sebustop® by Solabia;

linseed extracts, such as the product marketed under the trademark Linumine® by Lucas Meyer;

Phellodendron extracts, such as those marketed under the trademark Phellodendron extract BG by Maruzen or Oubaku liquid B by Ichimaru Pharcos;

mixtures of argan oil, of *Serenoa serrulata* (saw palmetto) extract and of sesame seed extract, such as the product marketed under the trademark Regu SEB® by Pentapharm;

mixtures of extracts of willowherb, of *Terminalia chebula*, of nasturtium and of bioavailable zinc (microalgae), such as the product marketed under the trademark Seborilys® by Green Tech;

extracts of *Pygeum afrianum*, such as the product marketed under the trademark *Pygeum afrianum* sterolic lipid extract by Euromed;

extracts of *Serenoa serrulata*, such as the products marketed under the trademark Viapure Sabal by Actives International or those marketed by Euromed;

mixtures of extracts of plantain, of *Berberis aquifolium* and of sodium salicylate, such as the product marketed under the trademark Seboclear® by Rahn;

clove extract, such as the product marketed under the trademark Clove extract powder by Maruzen;

argan oil, such as the product marketed under the trademark Lipofructyl® by Laboratoires Sérobiologiques;

lactic protein filtrates, such as the product marketed under the trademark Normaseb® by Sederma;

extracts of the alga *Laminaria*, such as the product marketed under the trademark Laminarghane® by Biotechmarine;

oligosaccharides of the alga *Laminaria digitata*, such as the product marketed under the trademark Phycosaccharide AC by Codif;

sugar cane extracts, such as the product marketed under the trademark Policosanol® by Sabinsa;

sulfonated shale oil, such as the product marketed under the trademark Ichthyol Pale® by Ichthyol;

European meadowsweet (*Spiraea ulmaria*) extracts, such as the product marketed under the trademark Cytobiol® Ulmaire by Libiol;

sebacic acid, especially marketed in the form of a sodium polyacrylate gel under the trademark Sebosoft® by Sederma;

glucomannans extracted from konjac tuber and modified with alkylsulfonate chains, such as the product marketed under the trademark Biopol Beta by Arch Chemical;

extracts of *Sophora angustifolia*, such as those marketed under the trademark Sophora powder or Sophora extract by Bioland;

extracts of *Cinchona succirubra* bark, such as the product marketed under the trademark Red Bark HS by Alban Muller;

extracts of *Quillaja saponaria*, such as the product marketed under the trademark Panama wood HS by Alban Muller;

glycine grafted onto an undecylenic chain, such as the product marketed under the trademark Lipacide UG OR by SEPPIC;

the mixture of oleanolic acid and of nordihydroguaiaretic acid, such as the product marketed in the form of a gel under the trademark AC.Net by Sederma;

phthalimidoperoxyhexanoic acid;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

10-hydroxydecanoic acid, and especially mixtures of 10-hydroxydecanoic acid, of sebacic acid and of 1,10-decanediol, such as the product marketed under the trademark Acnacidol® BG by Vincience; and mixtures thereof.

Preferred anti-seborrhoeic active agents include:

benzoyl peroxide and vitamin B6 (or pyridoxine), zinc salts such as zinc gluconate, zinc pyrrolidonecarboxy-late (or zinc pidolate), zinc lactate, zinc aspartate, zinc carboxylate, zinc salicylate and zinc cysteate;

meadowsweet (*Spiraea ulmaria*) extracts, such as the product marketed under the trademark Sebonormine® by Silab;

extracts of the alga *Laminaria saccharina*, such as the product marketed under the trademark Phlorogine-5 by Biotechmarine;

mixtures of extracts of salad burnet root (*Sanguisorba officinalis/Poterium officinale*), of ginger rhizomes (*Zingiber officinalis*) and of cinnamon bark (*Cinnamomum cassia*), such as the product marketed under the trademark Sebustop® by Solabia;

clove extract, such as the product marketed under the trademark Clove extract powder by Maruzen;

lactic protein filtrates, such as the product marketed under the trademark Normaseb® by Sederma;

European meadowsweet (*Spiraea ulmaria*) extracts, such as the product marketed under the trademark Cytobiol® Ulmaire by Libiol;

sebacic acid, especially marketed in the form of a sodium polyacrylate gel under the trademark Sebosoft® by Sederma;

glycine grafted onto an undecylenic chain, such as the product marketed under the trademark Lipacide UG OR by SEPPIC;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

10-hydroxydecanoic acid, and especially mixtures of 10-hydroxydecanoic acid, of sebacic acid and of 1,10-decanediol, such as the product marketed under the trademark Acnacidol® BG by Vincience; and mixtures thereof.

Preferentially, the anti-seborrhoeic active agent is selected from:

zinc salts such as zinc gluconate, zinc pyrrolidonecarboxylate (or zinc pidolate), zinc lactate, zinc aspartate, zinc carboxylate, zinc salicylate and zinc cysteate; and preferably zinc pyrrolidonecarboxylate (or zinc pidolate) or zinc salicylate;

clove extract, such as the product marketed under the trademark Clove extract powder by Maruzen;

glycine grafted onto an undecylenic chain, such as the product marketed under the trademark Lipacide UG OR by SEPPIC;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol; and mixtures thereof.

The anti-seborrhoeic active agent is, for example, present in a content ranging from 0.1% to 10% by weight, preferably from 0.1% to 5% by weight and preferentially from 0.5% to 3% by weight relative to the total weight of the composition.

Astringents:

According to the invention, the term "astringents" means agents for combating the dilation of the sebaceous follicles.

As astringents that may be included in the compositions according to the invention, exemplary are extracts of mushroom pulp (*Polyporus officinalis*), for instance Laricyl LS8865® from Cognis, extracts of *Terminalia catappa* and *Sambucus nigra*, for instance Phytofirm LS9120® from Cognis, extracts of gall nut, for instance Tanlex VE® from Ichimaru Pharcos, aluminum hydroxychloride, centella extracts (e.g. Plantactiv centella from Cognis), dicetyl dimethylammonium chloride, for instance Varisoft 432 CG® from Degussa, common horsechestnut extracts, mallow extracts, witch-hazel extracts, sweet almond extracts, marsh mallow root extracts and linseed extracts, for instance Almondermin LS 3380® from Cognis, burdock extracts, nettle extracts, birch extracts, horsetail extracts, camomile extracts, for instance those marketed under the trademark Extrapone 9 Special® by Symrise, skullcap extracts, European meadowsweet extracts (for example Cytobiol Ulmaire from Libiol), a mixture of extracts of white ginger, of horsetail, of nettle, of rosemary and of yucca, for instance Herb extract B1348® from Bell Flavors & Fragrances, extracts of acacia, of elm, of white willow, of cinnamon, of birch and of meadowsweet, Panama sapogenins, zinc phenolsulfonate from Interchemical, extracts of gentian, of cucumber and of walnut, the mixture of extracts of Ratanhia, of grapefruit, of gumweed and of oak gall, for instance Epilami® from Alban Muller.

Preferred astringents according to the invention, include skullcap extracts, European meadowsweet extracts, meadowsweet extracts, gentian extracts and burdock extracts, and mixtures thereof.

Cicatrizing Agents:

Examples of cicatrizing agents include:

allantoin, urea, certain amino acids, for instance hydroxyproline, arginine, and serine, and also extracts of white lily (for instance Phytélène Lys 37EG 16295 from Indena), a yeast extract, for instance the cicatrizing agent LS LO/7225B from Laboratoires Sérobiologiques), tamanu oil, extract of *Saccharomyces cerevisiae*, for instance Biodynes® TRF® from Arch Chemical, oat extracts, chitosan and derivatives, for instance chitosan glutamate, carrot extracts, artemia extract, for instance GP4G®E from Vincience, sodium acexamate, lavandin extracts, propolis extracts, ximeninic acid and salts thereof, rose hip oil, marigold extracts, for instance Souci Ami® Liposoluble from Alban Muller, horsetail extracts, lemon peel extracts, for instance Herbasol®) citron from Cosmetochem, helichrysum extracts, common yarrow extracts and folic acid.

Preferred cicatrizing agents according to the invention include arginine, serine, folic acid, tamanu oil, sodium acexamate, horsetail extracts and *helichrysum* extracts, and mixtures thereof.

Anti-Inflammatory Agents:

As particular anti-inflammatory agents according to the invention, exemplary are cortisone, hydrocortisone, indomethacin, betamethasone, azelaic acid, acetaminophen, diclofenac, clobetasol propionate, folic acid; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Preferred anti-inflammatory agents are azelaic acid, folic acid, an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Antiacne Agents:

In one advantageous embodiment of the invention, the composition may also comprise at least one anti-acne active.

The term "anti-acne active" especially means any active agent that has effects on the specific flora of greasy skin, for instance *Propionibacterium acnes* (*P. acnes*).

These effects may be bactericidal.

Antibacterial actives that are exemplary include:

actives and preservatives with antimicrobial activity mentioned in DE 103 24 567, which is incorporated into the present invention by reference, asiatic acid, the monoethanolamine salt of 1-hydroxy-4-methyl 6-trimethylpentyl-2-pyridone (INCI name: piroctone olamine), marketed especially under the trademark Octopirox® by Clariant;

citronellic acid, perillic acid (or 4-isopropenylcyclohex-1-enecarboxylic acid), glyceryl 2-ethylhexyl ether (INCI name: ethylhexylglycerine), for example marketed under the trademark Sensiva SC 50® by Schulke & Mayr, glyceryl caprylate/caprate, for example marketed under the trademark Capmul MCM® by Abitec;

sodium calcium phosphosilicate, especially marketed under the trademarks Bioactive Glasspowder® and Actysse Premier BG® by Schott Glass;

silver-based particles, for example those marketed under the trademark Metashine ME 2025 PS® by Nippon Sheet Glass;

hop cone extract (*Humulus lupulus*) obtained by supercritical $CO_2$ extraction, such as the product marketed under the trademark HOP CO2-TO extracts by Flavex Naturextrakte, St. John's Wort extract obtained by supercritical $CO_2$ extraction, such as the product marketed under the trademark St. John's Wort CO2-TO Extract® by Flavex Naturextrakte, the mixture of extracts of roots of *Scutellaria baicalensis*, of *Paeonia suffruticosa* and *Glycyrrhiza glabra*, such as the product marketed under the trademark BMB-CF® by Naturogin, argan tree extract, for instance Argapure LS9710® from Cognis;

bearberry leaf extracts, for instance the product marketed under the trademark Melfade-J by Pentapharm;

10-hydroxy-2-decanoic acid such as Acnacidol Po from Vincience, sodium ursolate, azelaic acid, diiodomethyl p-tolyl sulfone such as Amical Flowable® from Angus, malachite powder, zinc oxide such as Zincare® from Elementis GMBH, octadecenedioic acid such as Arlatone dioic DCA® from Uniqema; ellagic acid; 2,4,4'-trichloro-2'-hydroxydiphenyl ether (or triclosan), 1-(3', 4'-dichlorophenyl)-3-(4'-chlorophenyl)urea (or triclocarban), 3,4,4'-trichlorocarbanilide, 3',4',5'-trichlorosalicylanilide, phenoxyethanol, phenoxypropanol, phenoxyisopropanol, hexamidine isethionate, metronidazole and salts thereof, miconazole and salts thereof, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and salts thereof, benzoyl peroxide, 3-hydroxybenzoic acid, 4-hydroxybenzoic acid, phytic acid, N-acetyl-L-cysteine, lipoic acid, azelaic acid and salts thereof, arachidonic acid, resorcinol, 3,4,4'-trichlorocarbanalide, octoxyglycerine or octoglycerine, octanoylglycine such as Lipacid C8G® from SEPPIC, caprylyl glycol, 10-hydroxy-2-decanoic acid, dichlorophenylimidazoldioxolane and derivatives thereof described in WO 93/18743, iodopropynyl butylcarbamate, 3,7,11-trimethyldodeca-2,5,10-trienol or farnesol, phytosphingosines; quaternary ammonium salts, for instance cetyltrimethylammonium salts and cetylpyridinium salts, and mixtures thereof.

Also exemplary are certain surfactants with an antimicrobial effect, for instance sodium cocoamphoacetate or disodium diacetate such as Miranol C2M Conc. NP, betaines, for instance the cocoyl betaine Genagen KB from Clariant, sodium lauryl ether sulfate, for instance Emal 270 D from Kao, decyl glucoside, for instance Plantacare 2000 UP, branched $C_{12-13}$ dialkyl malates, for instance Cosmacol EMI, propylene glycol monoesters, for instance propylene glycol monolaurate, monocaprylate or monocaprate, lauryldimethylamine betaine, for instance Empigen BB/LS, and also polyquaternary ammoniums such as Quaternium-24 or Bardac 2050 from Lonza and those described in FR 0 108 283, and mixtures thereof.

Preferred antimicrobial agents are octoglycerine or octoxyglycerine, and 10-hydroxy-2-decanoic acid, and mixtures thereof.

Other additional anti-acne actives may be added to the abovementioned anti-acne actives.

Especially exemplary are actives with bacterial anti-adhesion effects or agents that act on the biofilm of bacteria to prevent them from multiplying.

As agents for preventing and/or reducing the adhesion of microorganisms, especially exemplary are:

phytantriol and derivatives thereof as described in EP-1-529,523, plant oils such as wheatgerm oil, calendula oil, castor oil, olive oil, avocado oil, sweet almond oil, groundnut oil, jojoba oil, sesame seed oil, apricot kernel oil, sunflower oil and *macadamia* oil, described in EP-1-133,979, or certain surfactants such as disodium cocoamphodiacetate, oxyethylenated (7 EO) glyceryl cocoate, 18-hexadecenyl succinate, octoxyglyceryl palmitate, octoxyglyceryl behenate, dioctyl adipate, PPG-15 stearyl ether, and the branched $C_{12}$-$C_{13}$ dialkyl tartrates described in EP-1-129,694, and mixtures thereof.

In particular with regard to the propagation of *P. acnes*, or as active agents that act on the biofilm of bacteria to prevent them from proliferating, exemplary are pentylene glycol, Nylon-66 (polyamide 66 fibers), rice bran oil, polyvinyl alcohol such as Celvol 540 PV Alcohol® from Celanese Chemical, rapeseed oil such as Akorex L® from Karlshamns, and fructose derivatives, and mixtures thereof.

The anti-acne active may be present in a content ranging from 0.01% to 10% by weight and preferably from 0.05% to 5% by weight relative to the total weight of the composition.

As a function of the nature and/or solubility of the abovementioned active agents, one skilled in this art will know how to select the most suitable embodiment according to the invention.

As lipophilic active agents that may be used in the kit or at least one of the compositions of the invention, especially exemplary are D-α-tocopherol, DL-α-tocopherol, D-α-tocopheryl acetate, DL-α-tocopheryl acetate, ascorbyl palmitate, vitamin F glycerides, D vitamins, vitamin D2, vitamin D3, retinol, retinol esters, retinyl palmitate, retinyl propionate, carotenes including β-carotene, D-panthenol, farnesol, farnesyl acetate, salicylic acid and derivatives thereof, for instance 5-n-octanoylsalicylic acid, α-hydroxy acid alkyl esters such as citric acid, lactic acid, glycolic acid, asiatic acid, madecassic acid, asiaticoside, the total extract of *Centella asiatica*, β-glycyrrhetinic acid, α-bisabolol, ceramides, for instance 2-oleoylamino-1,3-octadecane, phytantriol, phospholipids of marine origin rich in polyunsaturated essential fatty acids, ethoxyquine, rosemary extract, balm extract, quercetin, extract of dried microalgae, essential oil of bergamot, octyl methoxycinnamate, butylmethoxydibenzoylmethane, octyl triazone, 3,5-di-tert-butyl-4-hydroxy-3-benzylidenecamphor, antibiotics, antifungal agents, anaesthetics, analgesics, antiseptics, antiviral agents, pesticides and herbicides, and mixtures thereof.

The cosmetic and/or dermatological active agents will be present in the kit or one of the compositions according to the invention in a content ranging from 0.001% to 20% relative to the total weight of the composition, preferably from 0.01% to 10%, even more preferentially from 0.5% to 5% to more preferably from 0.1% to 1% by weight relative to the total weight of the composition.

For peeling applications, the contents of cosmetic and/or dermatological active agents may range from 1% to 50% by weight relative to the total weight of the composition and preferably from 1% to 30% by weight relative to the total weight of the composition.

Peels are a well-known means for improving the appearance and/or texture of the skin and/or the scalp, especially for improving the radiance and homogeneity of the complexion and/or for reducing the visible and/or tactile irregularities of the skin, and in particular for improving the surface appearance of the skin, for attenuating actinic lentigo, acne or chicken pox marks, and also for preventing, attenuating or combating the signs of aging of the skin, and especially for smoothing out irregularities in the texture of the skin, such as wrinkles and fine lines.

They have the effect of removing a surface part of the skin to be treated (epidermis and possibly the upper layer of the dermis), via chemical methods.

Other Additional Ingredients:

To complement and/or optimize the effects imparted by the cosmetic and/or dermatological actives mentioned above on the keratin materials, it may be advantageous to incorporate into the compositions of the invention other additional ingredients.

In particular, these additional ingredients may impart an immediate visual effect that will be taken up by the biological effect of the actives mentioned above. They may also, via a mechanical action (e.g.: abrasive fillers), amplify the effect of the biological actives mentioned above.

Thus, the compositions according to the invention may further comprise at least one agent selected from matting agents, soft-focus effect fillers, fluorescers, agents for promoting the naturally pinkish coloration of the skin, abrasive fillers or exfoliants, and mixtures thereof.

Matting Agents:

The term "matting agent" means agents intended to make the skin visibly more matt and less shiny.

The matting effect of the agent and/or composition containing it may especially be evaluated using a gonioreflectometer, by measuring the ratio R from the specular reflection and the scattered reflection. A value of R of less than or equal to 2 generally reflects a matting effect.

The matting agent may especially be selected from a rice starch or a corn starch, kaolinite, talc, a pumpkin seed extract, cellulose microbeads, plant fibers, synthetic fibers, in particular polyamide fibers, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that are especially representative include:
rice or corn starch, in particular an aluminum starch octenyl succinate marketed under the trademark Dry Flo® by National Starch;
kaolinite;
silicas;
talc;
a pumpkin seed extract as marketed under the trademark Curbilene® by Indena;
cellulose microbeads as described in EP-1-562,562;
fibers, such as silk fiber, cotton fiber, wool fiber, flax fiber, cellulose fiber extracted especially from wood, from vegetables or from algae, polyamide fiber (Nylon®), modified cellulose fiber, poly-p-phenyleneterephthamide fiber, acrylic fiber, polyolefin fiber, glass fiber, silica fiber, aramid fiber, carbon fiber, Teflon® fiber, insoluble collagen fiber, polyester fiber, polyvinyl chloride or polyvinylidene chloride fiber, polyvinyl alcohol fiber, polyacrylonitrile fiber, chitosan fiber, polyurethane fiber, polyethylene phthalate fiber, fibers formed from a mixture of polymers, resorbable synthetic fibers, and mixtures thereof described in EP-1-151,742;
expanded acrylic copolymer microspheres such as those marketed by EXPANCEL under the trademark Expancel 551®;
fillers with an optical effect as described in FR 2 869 796, in particular:
polyamide powders (Nylon®), for instance Nylon 12 particles of the Orgasol type from Arkema, with a mean size of 10 microns and a refractive index of 1.54,
silica powders, for instance Silica beads SB150 from Miyoshi with a mean size of 5 microns and a refractive index of 1.45,
polytetrafluoroethylene powders, for instance PTFE Ceridust 9205F from Clariant, with a mean size of 8 microns and a refractive index of 1.36,
silicone resin powders, for instance the silicone resin Tospearl 145A from GE Silicone with a mean size of 4.5 microns and a refractive index of 1.41,
acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles by Matsumoto Yushi-Seiyaku,
wax powders, for instance the paraffin wax particles Microease 114S from Micropowders, with a mean size of 7 microns and a refractive index of 1.54,
polyethylene powders, especially comprising at least one ethylene/acrylic acid copolymer, and in particular consisting of ethylene/acrylic acid copolymers, for instance the particles Flobeads EA 209 from Sumitomo (with a mean size of 10 microns and a refractive index of 1.48),
elastomeric crosslinked organopolysiloxane powders coated with silicone resin, especially with silsesquioxane resin, as described, for example, in U.S. Pat. No. 5,538,793. Such elastomeric powders are marketed under the trademarks KSP-100, KSP-101, KSP-102, KSP-103, KSP-104 and KSP-105 by Shin-Etsu, and
talc/titanium dioxide/alumina/silica composite powders such as those marketed under the trademark Coverleaf® AR-80 by Catalyst & Chemicals,
mixtures thereof,
compounds that absorb and/or adsorb sebum as described in FR 2 869 796. Mention may be made especially of:
silica powders, for instance the porous silica microspheres marketed under the trademark Silica Beads SB-700 marketed by Miyoshi, the products Sunsphere® H51, Sunsphere® H33 and Sunsphere® H53 marketed by Asahi Glass; the polydimethylsiloxane-coated amorphous silica microspheres marketed under the trademark SA Sunsphere® H-33 and SA Sunsphere® H-53 marketed by Asahi Glass;
amorphous mixed silicate powders, especially of aluminum and magnesium, for instance the product marketed under the trademark Neusilin UFL2 by Sumitomo;
polyamide (Nylon®) powders, for instance Orgasol® 4000 marketed by Arkema, and
acrylic polymer powders, especially of polymethyl methacrylate, for instance Covabead® LH85 marketed by Wackherr; of polymethyl methacrylate/ethylene glycol dimethacrylate, for instance Dow Corning 5640 Microsponge® Skin Oil Adsorber marketed by Dow Corning, or Ganzpearl® GMP-0820 marketed by Ganz Chemical; of polyallyl methacrylate/ethylene glycol dimethacrylate, for instance Poly-Pore® L200 or Poly-Pore® E200 marketed by Amcol; of ethylene glycol dimethacrylate/lauryl methacrylate copolymer, for instance Polytrap® 6603 marketed by Dow Corning;

silicate particles, such as alumina silicate;

mixed silicate particles, such as:

magnesium aluminum silicate particles, such as saponite or hydrated magnesium aluminum silicate with a sodium sulfate marketed under the trademark Sumecton® by Kunimine;

the magnesium silicate, hydroxyethylcellulose, black cumin oil, marrow oil and phospholipids complex or Matipure® from Lucas Meyer, and mixtures thereof.

Preferred matting agents according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

Fillers with a Soft-Focus Effect:

These fillers may be any material capable of modifying and hiding wrinkles by virtue of their intrinsic physical properties. These fillers may especially modify wrinkles via a tensioning effect, a covering effect or a soft-focus effect.

Examples of such fillers include the following compounds:

porous silica microparticles, for instance Silica Beads® SB150 and SB700 from Miyoshi with a mean size of 5 μm; the series-H Sunspheres® from Asahi Glass, for instance Sunspheres H33, H51 with respective sizes of 3.5 and 5 μm;

hollow hemispherical silicone resin particles such as NLK 500®, NLK 506® and NLK 510 from Takemoto Oil and Fat, especially described in EP-A-1-579,849;

silicone resin powders, for instance the silicone resin Tospearl® 145A from GE Silicone, with a mean size of 4.5 μm;

acrylic copolymer powders, especially of polymethyl (meth)acrylate, for instance the PMMA particles Jurimer MBI® from Nihon Junyoki, with a mean size of 8 μm, the hollow PMMA spheres marketed under the trademark Covabead® LH85 by Wackherr, and vinylidene/acrylonitrile/methylene methacrylate expanded microspheres marketed under the trademark Expancel®;

wax powders, for instance the paraffin wax particles MicroEase® 114S from MicroPowders, with a mean size of 7 μm;

polyethylene powders, especially comprising at least one ethylene/acrylic acid copolymer, for instance the Flobeads® EA 209 from Sumitomo, with a mean size of 10 μm;

crosslinked elastomeric organopolysiloxane powders coated with silicone resin and especially with silsesquioxane resin, marketed under the trademarks KSP-100®, KSP-101®, KSP-102®, KSP-1030, KSP-104® and KSP-105® by Shin-Etsu;

talc/titanium dioxide/alumina/silica composite powders, for instance Coverleaf AR 80® by Catalyst & Chemical;

talc, mica, kaolin, lauryl glycine, starch powders crosslinked with octenyl succinate anhydride, boron nitride, polytetrafluoroethylene powders, precipitated calcium carbonate, magnesium carbonate, magnesium hydrogen carbonate, barium sulfate, hydroxyapatite, calcium silicate, cerium dioxide and glass or ceramic microcapsules;

hydrophilic or hydrophobic, synthetic or natural, mineral or organic fibers such as silk fibers, cotton fibers, wool fibers, flax fibers, cellulose fibers extracted especially from wood, vegetables or algae, polyamide (Nylon®) fibers, modified cellulose fibers, poly-p-terephthamide fibers, acrylic fibers, polyolefin fibers, glass fibers, silica fibers, aramid fibers, carbon fibers, polytetrafluoroethylene (Teflon®) fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from a mixture of polymers, resorbable synthetic fibers, and mixtures thereof described in EP-1-151,742;

spherical elastomeric crosslinked silicones, for instance Trefil E-505C® or E-506C® from Dow Corning;

abrasive fillers, which, via a mechanical effect, smooth out the skin microrelief, such as abrasive silica, for instance Abrasif SP® from Semanez or nutshell powders (for example of apricot or walnut, from Cosmetochem).

The fillers with an effect on the signs of aging are especially selected from porous silica microparticles, hollow hemispherical silicone particles, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, magnesium hydrogen carbonate, barium sulfate, hydroxyapatite, calcium silicate, cerium dioxide, glass or ceramic microcapsules, and silk fibers or cotton fibers, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical.

The soft-focus fillers may be selected from silica and silicate powders, especially alumina powder, powders of polymethyl methacrylate (PMMA) type, talc, silica/$TiO_2$ or silica/zinc oxide composites, polyethylene powders, starch powders, polyamide powders, styrene/acrylic copolymer powders and silicone elastomers, and mixtures thereof.

Particularly exemplary is a talc with a number-average size of less than or equal to 3 microns, for example talc with a number-average size of 1.8 microns and especially the product marketed under the trademark Talc P3® by Nippon Talc, Nylon® 12 powder, especially the product marketed under the trademark Orgasol 2002 Extra D Nat Cos® by Atochem, silica particles 1% to 2% surface-treated with a mineral wax (INCI name: hydrated silica (and) paraffin) such as the products marketed by Degussa, amorphous silica microspheres, such as the products marketed under the trademark Sunsphere, for example of reference H-530 by Asahi Glass, and silica microbeads such as those marketed under the trademark SB-700® or SB-150® by Miyoshi, this list not being limiting.

The concentration of these fillers with an effect on the signs of aging in the compositions according to the invention may be from 0.1% to 40%, or even from 0.1% to 20% by weight, relative to the total weight of the composition.

Fluorescers:

The term "fluorescer" means a substance which, under the effect of ultraviolet rays and/or visible light, re-emits in the visible region the portion of light that it has absorbed under the same color as that which it naturally reflects. The naturally reflected color is thus reinforced by the re-emitted color and appears extremely bright.

Examples thereof include colored polyamide and/or formaldehyde/benzoguanamine and/or melamine/formaldehyde/ sulfonamide resins, from colored aminotriazine/formaldehyde/sulfonamide co-condensates and/or from metallized polyester flakes and/or mixtures thereof. These fluorescent pigments may also be present in the form of aqueous dispersions of fluorescent pigments.

Also exemplary are pink-colored fluorescent aminotriazine/formaldehyde/sulfonamide co-condensate with a mean particle size of 3-4 microns marketed under the trademark "Fiesta Astral Pink FEX-1" and the blue-colored fluorescent aminotriazine/formaldehyde/sulfonamide co-condensate with a mean particle size of 3-4.5 microns marketed under the trademark "Fiesta Comet Blue FTX-60" by Swada, or, alternatively, the yellow-colored benzoguanamine/formaldehyde resin covered with formaldehyde/urea resin marketed under the trademark "FB-205 Yellow" and the red-colored benzoguanamine/formaldehyde resin covered with formaldehyde/urea resin marketed under the trademark "FB-400 Orange Red" by UK Seung Chemical, and the orange-colored polyamide resin marketed under the trademark "Flare 911 Orange 4" by Sterling Industrial Colors.

The fluorescent substances are preferably present in the composition in a content ranging from 0.1% to 20%, preferably from 0.1% to 15% to more preferably from 0.5% to 3% by weight relative to the total weight of the composition.

When the organic fluorescent substances are white, they are also known as optical brighteners.

The optical brightener has the effect of intensifying the radiance and reviving the shades of cosmetic compositions comprising them on application to the skin.

Among the optical brighteners that are more particularly exemplary are stilbene derivatives, in particular polystyrylstilbenes and triazinestilbenes, coumarin derivatives, in particular hydroxycoumarins and aminocoumarins, oxazole, benzoxazole, imidazole, triazole and pyrazoline derivatives, pyrene derivatives and porphyrin derivatives, and/or mixtures thereof.

Such compounds are available, for example, under the trademarks Tinopal SOP® and Uvitex OB® by Ciba Geigy.

The optical brighteners preferentially used are sodium 4,4'-bis[(4,6-dianilino-1,3,5-triazin-2-yl)amino]stilbene-2,2'-disulfonate, 2,5-thiophenediylbis(5-tert-butyl-1,3-benzoxazole) and disodium 4,4'-distyrylbiphenylsulfonate, and/or mixtures thereof.

Agents for Promoting the Naturally Pinkish Coloration of the Skin:

Especially exemplary are:
a self-tanning agent, i.e., an agent which, when applied to the skin, especially to the face, can produce a tan effect that is more or less similar in appearance to that which may result from prolonged exposure to the sun (natural tan) or under a UV lamp;
an additional coloring agent, i.e., any compound that has a particular affinity for the skin, which allows it to give the skin a lasting, non-covering coloration (i.e., that does not have a tendency to opacify the skin) and that is not removed either with water or using a solvent, and that withstands both rubbing and washing with a solution containing surfactants. Such a lasting coloration is thus distinguished from the superficial and transient coloration provided, for example, by a makeup pigment; and mixtures thereof.

Examples of Self-Tanning Agents Include:
dihydroxyacetone (DHA),
erythrulose, and
the combination of a catalytic system formed from:
manganese and/or zinc oxide salts, and
alkali metal and/or alkaline-earth metal hydrogen carbonates.

The self-tanning agents are generally selected from monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in FR 2,466,492 and WO 97/35842, dihydroxyacetone (DHA) and 4,4-dihydroxypyrazolin-5-one derivatives as described in EP-903,342. DHA will preferably be used.

The DHA may be used in free and/or encapsulated form, for example in lipid vesicles such as liposomes, especially described in WO 97/25970.

In general, the self-tanning agent is present in an amount ranging from 0.01% to 20% by weight and preferably in an amount of from 0.1% to 10% of the total weight of the composition.

Other dyes that allow modification of the color produced by the self-tanning agent may also be used.

These dyes may be selected from synthetic or natural direct dyes.

These dyes may be selected, for example, from red or orange dyes of the fluoran type such as those described in FR 2,840,806.

Exemplary are the following dyes:
tetrabromofluoresceine or eosin known under the CTFA name: CI-45380 or Red 21;
phioxin B known under the CTFA name: C145410 or Red 27;
diiodofluoresceine known under the CTFA name: C145425 or Orange 10;
dibromofluoresceine known under the CTFA name: C145370 or Orange 5;
the sodium salt of tetrabromofluoresceine known under the CTFA name: C145380 (Na salt) or Red 22;
the sodium salt of phloxin B known under the CTFA name: C145410 (Na salt) or Red 28;
the sodium salt of diiodofluoresceine known under the CTFA name: C145425 (Na salt) or Orange 11;
erythrosine known under the CTFA name: C145430 or Acid Red 51;
phloxin known under the CTFA name: C145405 or Acid Red 98.

These dyes may also be selected from anthraquinones, caramel, carmine, carbon black, azulene blues, methoxalene, trioxalene, guajazulene, chamuzulene, Bengal rose, cosin 10B, cyanosin and daphinin.

These dyes may also be selected from indole derivatives, for instance the monohydroxyindoles as described in FR 2 651 126 (i.e., 4-, 5-, 6- or 7-hydroxyindole) or the dihydroxyindoles as described in EP-B-0,425,324 (i.e., 5,6-dihydroxyindole, 2-methyl-5,6-dihydroxyindole, 3-methyl-5,6-dihydroxyindole or 2,3-dimethyl-5,6-dihydroxyindole).

Abrasive Fillers or Exfoliants:

As exfoliants that may be included in rinse-out compositions according to the invention, examples thereof include exfoliant or scrubbing particles of mineral, plant or organic origin. Thus, polyethylene beads or powder, Nylon powder, polyvinyl chloride powder, pumice powder, ground apricot kernel or walnut shell, sawdust, glass beads and alumina, and mixtures thereof, may be used, for example.

Also exemplary are Exfogreen® from Solabia (bamboo extract), extracts of strawberry akenes (Strawberry Akenes from Greentech), peach kernel powder, apricot kernel powder, and finally, in the field of plant powders with an abrasive effect, mention may be made of cranberry kernel powder.

As abrasive fillers or exfoliants that are preferred according to the invention, exemplary are peach kernel powder, apricot kernel powder, cranberry kernel powder, strawberry akene extracts and bamboo extracts.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES of PREPARATION of
SEMI-CRYSTALLINE POLYMERS

Example 1

Acidic Polymer with Melting Point of 40° C.

A 1 l reactor equipped with a central stirrer with anchor, a condenser and a thermometer is charged with 120 g of Parléam® oil (mineral oil), which is heated from the ambient temperature to 80° C. over 45 minutes. At 80° C., over 2 hours, the following mixture $C_1$ is introduced:

40 g of cyclohexane+4 g of Triganox 141 [2,5-bis(2-ethylhexanoylperoxy)-2,5-dimethylhexane].

30 minutes after the beginning of the feed of the mixture $C_1$, the mixture $C_2$ is introduced over 1 hour 30 minutes, this mixture being constituted of:

190 g of stearyl acrylate+10 g of acrylic acid+400 g of cyclohexane.

At the end of the two feeds, the batch is allowed to react for 3 hours more at 80° C., and then all of the cyclohexane present in the reaction mixture is distilled off under atmospheric pressure.

This gives the polymer at 60% by weight of active ingredient in Parléam® oil.

Its weight-average molecular mass $M_w$ is 35,000 expressed as a polystyrene equivalent, and its melting temperature m.p. is 40° C.±1° C. as measured by DSC.

Example 2

Basic Polymer with Melting Point of 38° C.

The same procedure is employed as in Example 1, except that N-vinylpyrrolidone is used instead of the acrylic acid.

The resulting polymer is at 60% by weight of active ingredient in Parleam® oil, its weight-average molecular mass $M_w$ is 38,000 and its m.p. is 38° C.

Example 3

Acidic Polymer with Melting Point of 60° C.

The same procedure is employed as in Example 1, except that behenyl acrylate is used instead of the stearyl acrylate. The resulting polymer is at 60% by weight of active ingredient in Parléam® oil. Its weight-average molecular mass $M_w$ is 42,000 and its m.p. is 60° C.

Example 4

Basic Polymer with Melting Point of 58° C.

The same procedure is employed as in Example 2, except that behenyl acrylate is used instead of the stearyl acrylate.

The resulting polymer is at 60% by weight of active ingredient in Parléam® oil. Its weight-average molecular mass $M_w$ is 45,000 and its m.p. is 58° C.

II) Composition Examples 1 to 4

| Ingredients | Ex. 1 | Ex. 2* | Ex. 3* | Ex. 4* |
|---|---|---|---|---|
| Phase $A_1$ | | | | |
| Disodium EDTA | 0.1 | 0.1 | 0.1 | 0.1 |
| Preservative | 1.25 | 1.25 | 1.25 | 1.25 |
| Glycerol | 4 | 4 | 4 | 4 |
| Propylene glycol | 4 | 4 | 4 | 4 |
| Water | 61.65 | 61.65 | 61.65 | 61.65 |
| Phase $A_2$ | | | | |
| Particle dispersion containing 86% by weight Styrene/Acrylates Copolymer (Sunspheres Powder from Rohm & Haas) | 2 | 2 | — | — |
| Phase $B_1$ | | | | |
| Poly($C_{10}$-$C_{30}$)alkyl acrylates (Intelimer 13-1 from Landec) | 1 | — | 1 | — |
| Mixture of glycerol stearate, behenyl alcohol, sodium sulfate of dicocoylethylenediamine PEG-15, glyceryl citrate stearate | 2 | 2 | 2 | 2 |
| Isononyl isononanoate | 4 | 4 | 4 | 4 |
| Cetyl alcohol | 0.5 | 0.5 | 0.5 | 0.5 |
| Butylmethoxy Dibenzoylmethane | 3 | 3 | 3 | 3 |
| Ethylhexyl Salicylate | 5 | 5 | 5 | 5 |
| Octocrylene | 7 | 7 | 7 | 7 |
| Phase $B_2$ | | | | |
| Fragrance | 0.4 | 0.4 | 0.4 | 0.4 |
| Tocopherol | 0.2 | 0.2 | 0.2 | 0.2 |
| Acrylates Copolymer | 0.7 | 0.7 | 0.7 | 0.7 |
| Phase D | | | | |
| Triethanolamine | 0.2 | 0.2 | 0.2 | 0.2 |

*outside the invention

For each of compositions 1 to 4 the mean in vivo SPF is measured on 5 subjects in accordance with the international COLIPA 2003 method.

The results obtained are shown in the following table:

| | Ex. 1 | Ex. 2* | Ex. 3* | Ex. 4* |
|---|---|---|---|---|
| Number of subjects | 5 | 5 | 5 | 5 |
| Mean in vivo SPF | 29.5 | 11.8 | 9.8 | 4.8 |

*outside the invention

It is observed that, in composition 1 according to the invention, the semi-crystalline polymer/hollow latex particles combination leads to synergy in terms of the SPF relative to each of the components used alone, respectively, in compositions 2 and 3.

The mean SPF of composition 1 (29.5) is greater by 35% than the sum (21.6) of the mean SPFs of compositions 2 and 3.

The mean SPF of composition 1 (29.5) is 6 times greater than the SPF of composition 4 (4.8), which contains none of the components of the combination.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological UV protection composition having enhanced SPF which comprises at least one organic UV screening agent and/or at least one inorganic screening agent, said composition further comprising at least the following constituents (A) and (B):
   A) a semi-crystalline polymer which is solid at ambient temperature and has a melting point of greater than or equal to 30° C., containing a) a polymeric backbone and b) at least one crystallizable organic side chain and/or one crystallizable organic block forming part of the backbone of said polymer, and said polymer having a number-average molecular mass Mn of greater than or equal to 1,000 g/mol, wherein said polymer is selected from the group consisting of poly(stearyl acrylate)s, and
   B) hollow latex particles having a particle size ranging from 150 to 380 nm, wherein said latex particles comprise a copolymer of styrene and (meth)acrylic acid or one of its $C_1$-$C_{20}$ alkyl esters, formulated into a topically applicable, physiologically acceptable medium therefor.

2. The cosmetic/dermatological UV protection composition as defined by claim 1, said semi-crystalline polymer having a melting point ranging from 30° C. to 80° C.

3. The cosmetic/dermatological UV protection composition as defined by claim 1, said semi-crystalline polymer having a number-average molecular mass Mn ranging from 2,000 to 800,000 g/mol.

4. The cosmetic/dermatological UV protection composition as defined by claim 1, said semi-crystalline polymer having been obtained from a monomer having a crystallizable chain and selected from among saturated $C_{14}$ to $C_{22}$ alkyl (meth)acrylates.

5. The cosmetic/dermatological UV protection composition as defined by claim 1, said semi-crystalline polymer being present in an amount ranging from 0.1% to 50% by weight, relative to the total weight thereof.

6. The cosmetic/dermatological UV protection composition as defined by claim 1, said hollow latex particles having a particle size ranging from 150 to 375 nm.

7. The cosmetic/dermatological UV protection composition as defined by claim 1, said hollow latex particles having been obtained from particles comprising at least one polymer for the core and at least one polymer for the shell.

8. The cosmetic/dermatological UV protection composition as defined by claim 7, wherein the monomers polymerized for the shell of the latex particles comprise one or more unsaturated nonionic ethylenic units and optionally one or more monoethylenically unsaturated monomers containing at least one carboxylic acid group.

9. The cosmetic/dermatological UV protection composition as defined by claim 7, wherein the monomers polymerized into the core polymer of the latex particles comprise one or more monoethylenically unsaturated monomers containing at least one carboxylic acid group.

10. The cosmetic/dermatological UV protection composition as defined by claim 7, said hollow latex particles being present in amounts ranging from 0.1% to 20% by weight, relative to the total weight thereof.

11. The cosmetic/dermatological UV protection composition as defined by claim 1, comprising at least one organic UV screening agent or agents selected from the group consisting of cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives; benzimidazole derivatives; imidazolines; bisbenzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene-derived dimers; 4,4-diarylbutadienes; merocyanin derivatives; and mixtures thereof.

12. The cosmetic/dermatological UV protection composition as defined by claim 1, comprising at least one inorganic screening agent or agents which comprise coated or uncoated oxide pigments of titanium, zinc, iron, zirconium, cerium, or their mixtures having an average elementary particle size of less than or equal to 500 nm.

13. A regime or regimen for UV photoprotecting the skin, lips, nails, hair, scalp, lashes and/or brows against the damaging effects of UV radiation, comprising topically applying thereon an enhanced SPF effective amount of the cosmetic/dermatological UV protection composition as defined by claim 1.

14. The cosmetic/dermatological UV protection composition as defined by claim 1, further comprising at least one further active agent selected from the group consisting of moisturizers, desquamating agents, agents improving the skin barrier function, depigmenting agents, antioxidants, dermo-decontracting agents, anti-glycation agents, agents stimulating the synthesis of dermal and/or epidermal macromolecules and/or preventing their degradation, agents stimulating fibroblast or keratinocyte proliferation and/or keratinocyte differentiation, agents promoting the maturation of the horny envelope, NO synthase inhibitors, peripheral benzodiazepine receptor (PBR) antagonists, agents increasing the activity of the sebaceous gland, agents stimulating the energy metabolism of cells, tensioning agents, fat restructuring agents, slimming agents, agents promoting the cutaneous microcirculation, calmatives and/or anti-irritants, sebo-regulating or anti-seborrheic agents, astringents, cicatrizing agents, anti-inflammatory agents and anti-acne agents.

15. The cosmetic/dermatological UV protection composition as defined by claim 1, further comprising at least one further active agent selected from the group consisting of matting agents, soft-focus effect fillers, fluorescers, agents promoting the naturally pinkish coloring of the skin, abrasive fillers and exfoliants.

* * * * *